(12) United States Patent
Ogasawara et al.

(10) Patent No.: US 11,234,613 B2
(45) Date of Patent: Feb. 1, 2022

(54) RESPIRATION ESTIMATION METHOD AND APPARATUS

(71) Applicant: NIPPON TELEGRAPH AND TELEPHONE CORPORATION, Tokyo (JP)

(72) Inventors: Takayuki Ogasawara, Kanagawa (JP); Takurou Tajima, Kanagawa (JP); Kei Kuwabara, Kanagawa (JP); Nobuaki Matsuura, Tokyo (JP); Ryoichi Kasahara, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 665 days.

(21) Appl. No.: 15/778,750

(22) PCT Filed: Nov. 25, 2016

(86) PCT No.: PCT/JP2016/084978
§ 371 (c)(1),
(2) Date: May 24, 2018

(87) PCT Pub. No.: WO2017/090732
PCT Pub. Date: Jun. 1, 2017

(65) Prior Publication Data
US 2018/0344208 A1    Dec. 6, 2018

(30) Foreign Application Priority Data

Nov. 25, 2015 (JP) .............................. JP2015-229360
Jul. 29, 2016 (JP) .............................. JP2016-149625

(51) Int. Cl.
*A61B 5/08* (2006.01)
*A61B 5/0205* (2006.01)
(Continued)

(52) U.S. Cl.
CPC .......... *A61B 5/0816* (2013.01); *A61B 5/0205* (2013.01); *A61B 5/08* (2013.01);
(Continued)

(58) Field of Classification Search
CPC ..... A61B 5/0816; A61B 5/0205; A61B 5/113; A61B 5/08; A61B 5/7203; A61B 5/7257;
(Continued)

(56) References Cited

U.S. PATENT DOCUMENTS 6,413,223 B1 *   7/2002   Yang ....................... A61B 5/021
                                                             600/485
2010/0179438 A1 *  7/2010  Heneghan ............... A61B 5/113
                                                             600/484
(Continued)

FOREIGN PATENT DOCUMENTS

EP      1463447 A1      10/2004
JP      06-189009 A      7/1994
(Continued)

OTHER PUBLICATIONS

Foussier et al., An adaptive Kalman filter approach for cardiorespiratory signal extraction and fusion of non-contacting sensors. BMC Med Inform Decis Mak 14, 37 (Year: 2014).*
(Continued)

*Primary Examiner* — Jacqueline Cheng
*Assistant Examiner* — Tho Q Tran
(74) *Attorney, Agent, or Firm* — Womble Bond Dickinson (US) LLP

(57) ABSTRACT

There is provided a respiration estimation method. The respiration estimation method includes a first step (S107) of estimating a breathing rate of a subject based on each of a time-series signal of first data relating to a cardiac function of the subject and a time-series signal of second data relating to an acceleration by a respiratory motion of the subject, a
(Continued)

second step (S108) of estimating a breathing rate obtained by filtering noise using a Kalman filter for each of the breathing rate estimated based on the first data and the breathing rate estimated based on the second data, and a third step (S109) of executing weighted averaging processing for the plurality of estimated values of the breathing rates obtained in the second step.

11 Claims, 21 Drawing Sheets

(51) Int. Cl.
  *A61B 5/113* (2006.01)
  *A61B 5/00* (2006.01)
  *A61B 5/349* (2021.01)
  *A61B 5/087* (2006.01)

(52) U.S. Cl.
  CPC .............. *A61B 5/087* (2013.01); *A61B 5/113* (2013.01); *A61B 5/349* (2021.01); *A61B 5/7203* (2013.01); *A61B 5/725* (2013.01); *A61B 5/7221* (2013.01); *A61B 5/7257* (2013.01); *A61B 5/0803* (2013.01)

(58) Field of Classification Search
  CPC ....... A61B 5/7221; A61B 5/087; A61B 5/725; A61B 5/0452; A61B 5/0803
  USPC .......................................................... 600/529
  See application file for complete search history.

(56) References Cited

U.S. PATENT DOCUMENTS

| | | | |
|---|---|---|---|
| 2014/0228692 A1 | 8/2014 | Chan et al. | |
| 2016/0021613 A1 | 1/2016 | Mani et al. | |
| 2016/0220128 A1* | 8/2016 | Den Brinker | ........ A61B 5/0008 |

FOREIGN PATENT DOCUMENTS

| | | |
|---|---|---|
| JP | 2006-068091 A | 3/2006 |
| JP | 2008-085608 A | 4/2008 |
| JP | 2012-055604 A | 3/2012 |
| JP | 2013-085702 A | 5/2013 |
| JP | 2013-140529 A | 7/2013 |
| JP | 2013-186621 A | 9/2013 |
| JP | 2015-083045 A | 4/2015 |
| WO | 03/51198 A1 | 6/2003 |

OTHER PUBLICATIONS

Office Action received for Japanese Patent Application No. 2018-518237, dated Dec. 28, 2018, 6 pages (3 pages of English Translation and 3 pages of Office Action).
Office Action received for Japanese Patent Application No. 2017-552730, dated Dec. 25, 2018, 7 pages (3 pages of English Translation and 4 pages of Office Action).
Yoshida et al., "Estimation of Respiration Variability by Heart Rate Time Series", Transactions of Japanese Society for Medical and Biological Engineering, 2005, vol. 43, No. 3, pp. 456-460.
Yoon et al., "Improvement of Dynamic Respiration Monitoring Through Sensor Fusion of Accelerometer and Gyro-sensor", J. Electr. Eng. Technol., 2013, vol. 8, pp. 742-751.
Nemati et al., "Data Fusion for Improved Respiration Rate Estimation", EURASIP Journal on Advances in Signal Processing, 2010, vol. 2010, Article ID 926305, 10 pages.
Luo et al., "Multisensor fusion and integration: approaches, applications, and future research directions", IEEE Journal Sensor, vol. 2, No. 2, Apr. 2002, pp. 107-119.
Li et al., "Robust heart rate estimation from multiple asynchronous noisy sources using signal quality indices and a Kalman filter", Physiological Measurement, vol. 29, 2008, pp. 15-32.
Lepine et al., "Robust Respiration Rate Estimation Using Adaptive Kalman Filtering with Textile ECG Sensor and Accelerometer", 2016 38th Annual International Conference of the IEEE Engineering in Medicine and Biology Society (EMBC), 2016, pp. 3797-3800.
Johnson et al., "Improved Respiration Rate Estimation Using a Kalman Filter and Wavelet Cross-Coherence", Computing in Cardiology, 2013, vol. 40, pp. 791-794.
International Search Report and Written Opinion received for PCT Patent Application No. PCT/JP2016/084978, dated Feb. 21, 2017, 17 pages (9 pages of English Translation and 8 pages of Original Document).
International Preliminary Report on Patentability received for PCT Patent Application No. PCT/JP2016/084978, dated Jun. 7, 2018, 15 pages (9 pages of English Translation and 6 pages of Original Document).
Chung, Peter, "ECG Implementation on the TMS320C5515 DSP Medical Development Kit (MDK) with the ADS 1298 ECG-FE", Texas Instruments, Application Report, SPRABJ1, Jan. 2011, 20 pages.
Chan et al., "Ambulatory Respiratory Rate Detection using ECG and a Triaxial Accelerometer", 35th Annual International Conference of the IEEE EMBS, 2013, pp. 4058-4061.
Bates et al., "Respiratory rate and flow waveform estimation from tri-axial accelerometer data", International Conference on Body Sensor Networks, 2010, pp. 144-150.
European Search Report and Search Opinion received for EP Patent Application No. 16868675.6, dated Jul. 15, 2020, 8 pages.

* cited by examiner

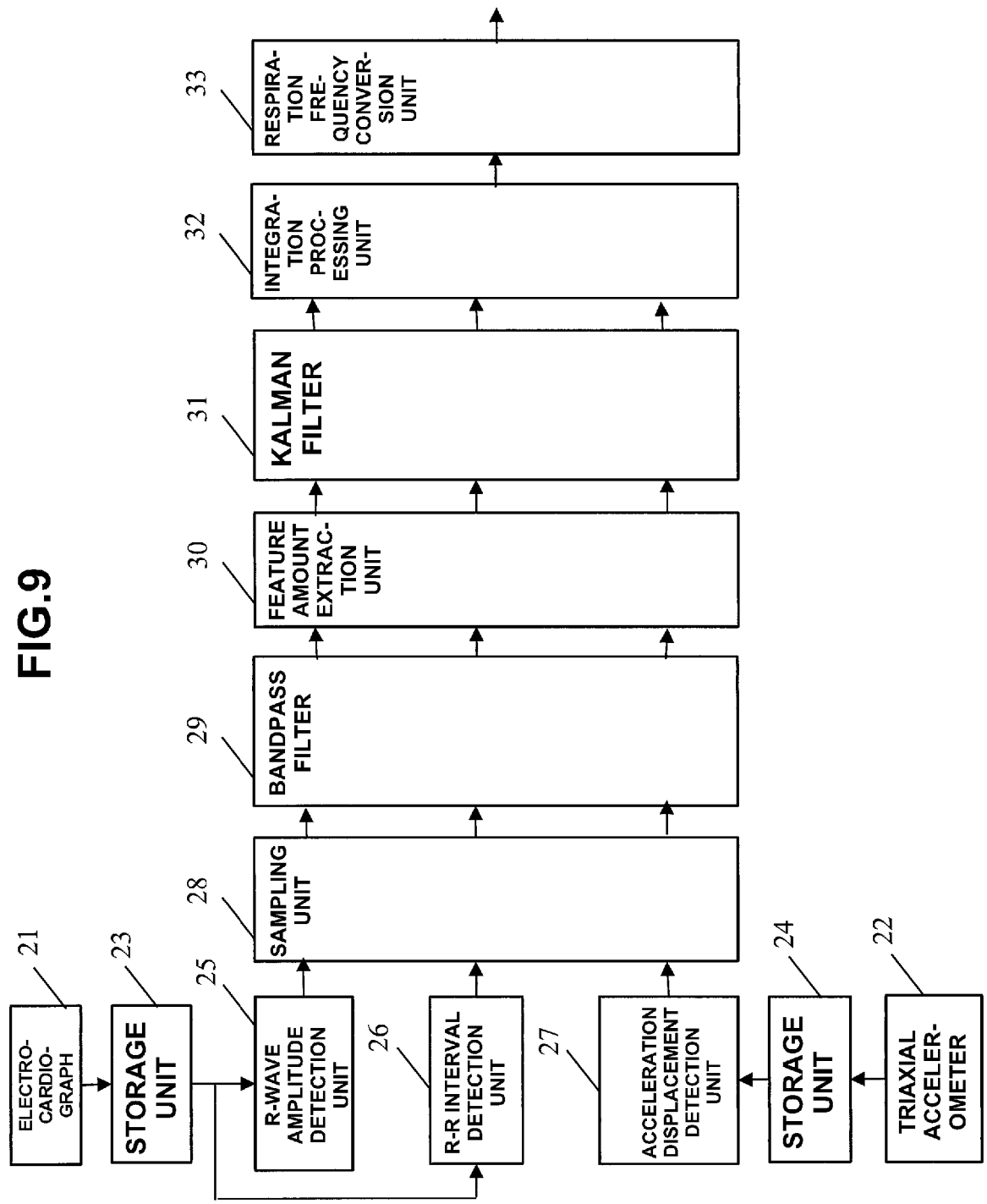

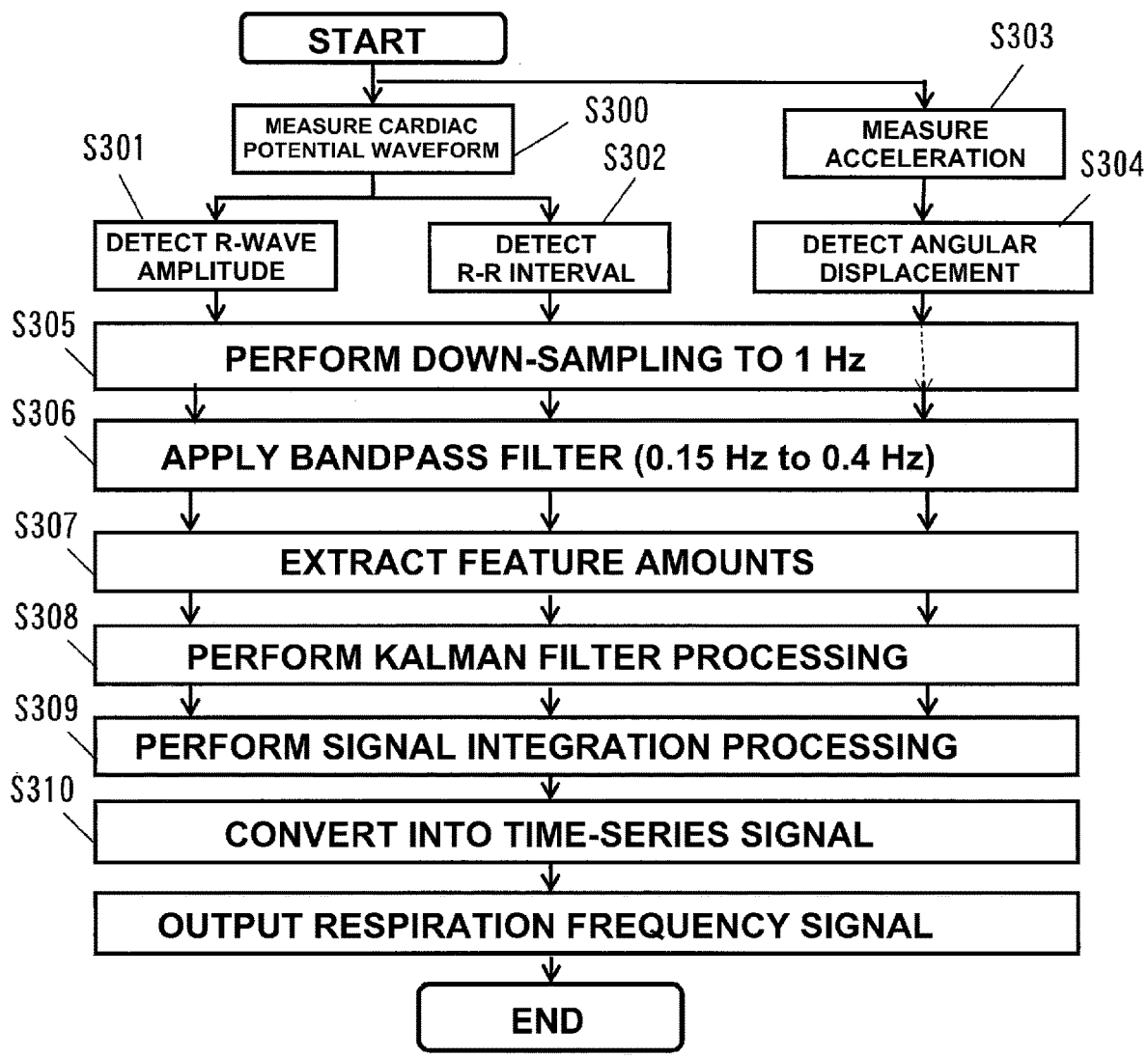

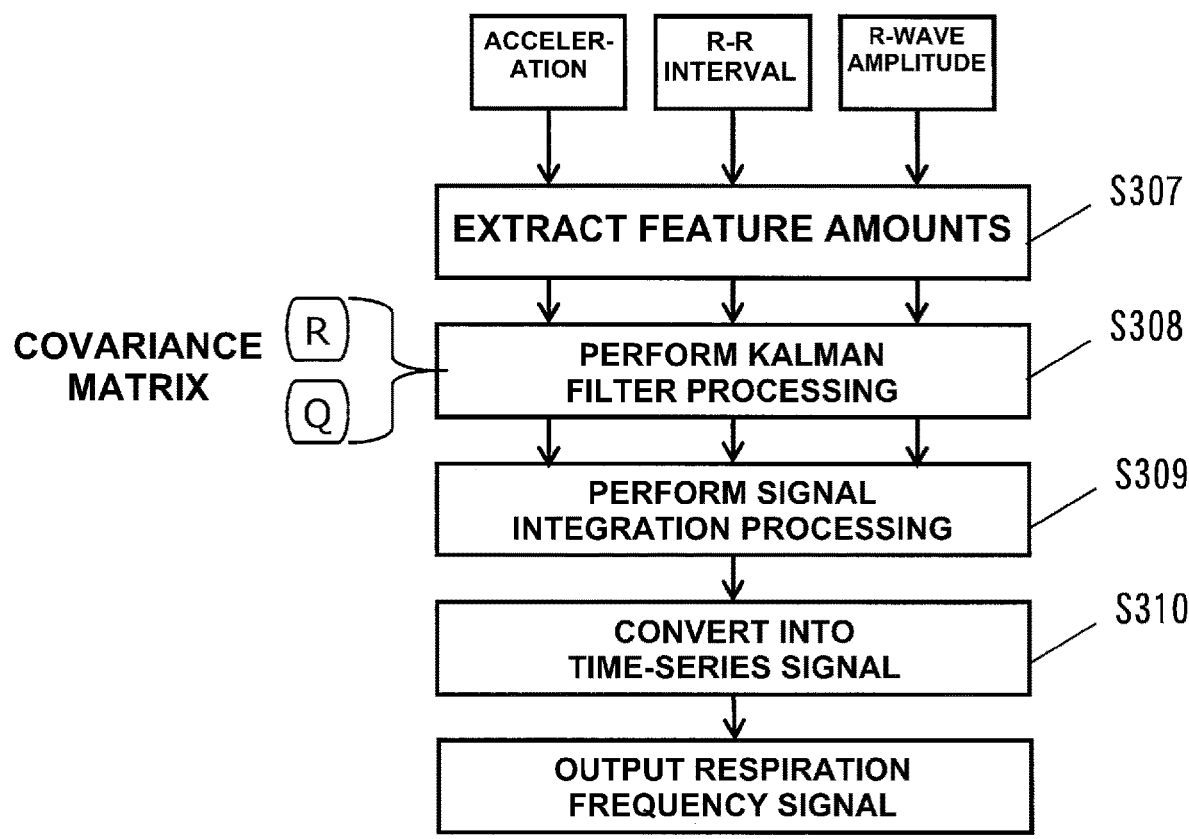

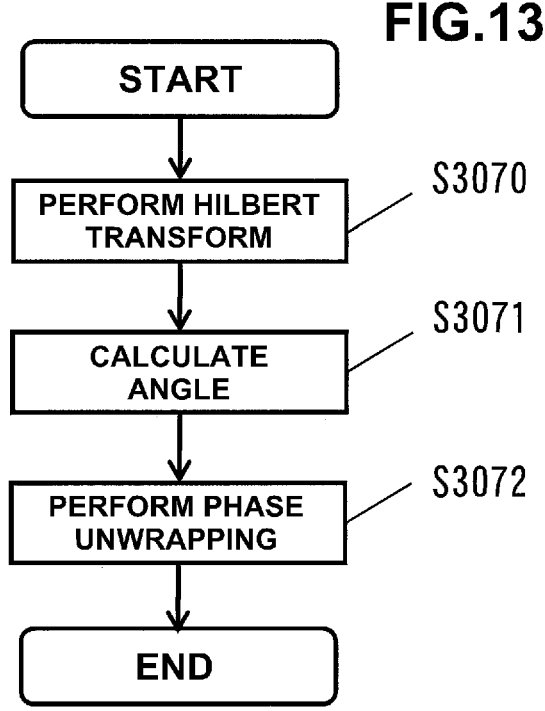
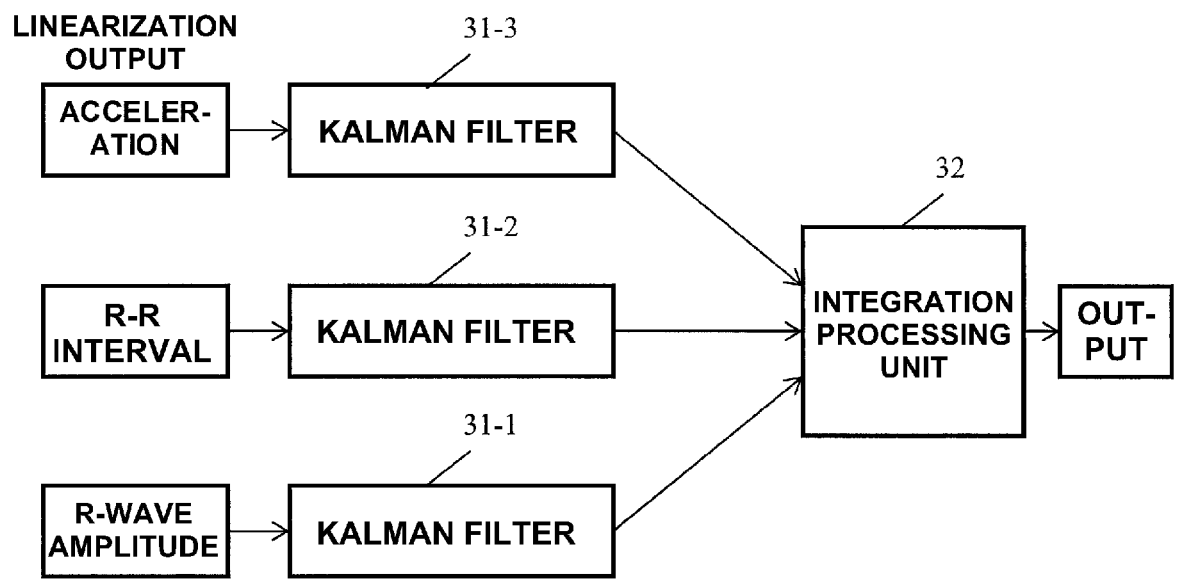

RESPIRATION ESTIMATION METHOD AND APPARATUS

TECHNICAL FIELD

The present invention relates to a respiration estimation method and apparatus for estimating the respiration condition of a subject using a biological information sensor.

BACKGROUND ART

Continuous respiratory monitoring of continuously observing breathing of a person is expected to be applied to diagnosis of respiratory diseases, the rehabilitation of a patient with a respiratory disease, remote monitoring of a fetus or patient, stress diagnosis, and the like. As a general respiration measurement method, a respiratory flow meter by a mask, heat measurement by a thermistor arranged in the nasal cavity, a chest deflection measurement band, an electrical impedance meter for a chest, or the like is used. These methods pose a problem that a subject has an unnatural feeling when wearing the device.

On the other hand, in recent years, along with the progress of wearable devices, there have been devices that are developed to give an improved wearing feeling to a human body. For example, there is proposed a wearable sensor in which electrodes 101 and 102 are embedded in clothing 100 such as a shirt, as shown in FIG. 22 (patent literature 1). This wearable sensor functions as a wearable electrocardiograph by arranging, near a heart 103, the electrodes 101 and 102 made of conductive fiber, and connecting the electrodes 101 and 102 to terminals (not shown) via wiring lines.

An attempt has been made to estimate the respiration condition of a person from a cardiac potential. However, when an attempt is made to estimate the respiration condition of a subject using an R-R interval as the interval between the R wave and the immediately preceding R wave of a cardiac potential, the influence of the autonomic nervous system of the subject becomes significantly apparent, and an estimation result changes depending on the age of the subject or the mental condition of the subject at the time of measurement or whether it is before or after the measurement. When an attempt is made to estimate the respiration condition of a subject using the R-wave amplitude of a cardiac potential, a measurement error occurs in accordance with a change in contact impedance between the electrode and the skin, that is caused by the body motion or skin condition of the subject, or the individual difference of the body structure or skin condition of the subject.

Thus, for example, non-patent literature 1 discloses a method of estimating the respiration condition (breathing rate) of a subject based on acceleration data of the subject in addition to conventional electrocardiograph data. The method disclosed in non-patent literature 1 improves estimation accuracy by obtaining the weighted mean of three indices of the R-R interval, R-wave amplitude, and acceleration of a cardiac potential. In the method disclosed in non-patent literature 1, when $BR_{RSA}$ represents a respiratory rate estimated from the R-R interval, $BR_{QRsa}$ represents a respiratory rate estimated from the R-wave amplitude, and $BR_{accel}$ represents a respiratory rate estimated from the acceleration data, a respiratory rate $BR_{combined}$ obtained by the weighted mean of the above respiratory rates is given by:

$$BR_{combined} = (Q_{RSA}BR_{RSA} + Q_{QRsa}BR_{QRsa} + Q_{accel}BR_{QRSa})/(Q_{RSA} + Q_{QRsa} + Q_{accel}) \quad (1)$$

The weighting constants $Q_{RSA}$, $Q_{QRSa}$ and $Q_{accel}$ of equation (1) change depending on the respective indices of the R-R interval, R-wave amplitude, and acceleration, and are adjusted within the range of 0 to 1 depending on the signal quality. By peak detection of time-series data, an error constant E is calculated as the linear sum of four parameters, that is, the standard deviation of peak amplitudes, the average value of the peak amplitudes, a time-varying constant between minimum values, and the ratio between the number of maximum and minimum values and the total number of maximum and minimum values, and signal quality Q is given by:

$$Q = \exp\{-(E/\tau)\} \quad (2)$$

where $\tau$ represents an empirically determined constant. Note that if the signal amplitude is set as a noise level, Q is set to zero.

As for robust integration calculation processing using a plurality of sensors, there is known a method using a Kalman filter in the fields of robot control, biomedical treatment, apparatus monitoring, and the like (non-patent literature 2). Integration processing based on a Kalman filter is applied to a robust measurement of a heart rate using an electrocardiographic waveform and an arterial pressure in the field of biomedical treatment (non-patent literature 3).

In the method disclosed in non-patent literature 1, since a respiratory sampling interval is restricted by the cardiac cycle, it is difficult to measure a pneumogram with a short cycle. Furthermore, in the method disclosed in non-patent literature 1, variations of the R-wave amplitude of the cardiac potential and variations of the signal waveform amplitude of the accelerator also occur due to an artifact caused by the body motion of the subject, and the constant T to be used to calculate the respiratory rate needs to be changed in accordance with the individual difference. Hence, the SN (Signal-to-Noise) ratio does not always improve, and respiration estimation accuracy cannot be improved.

Furthermore, in a field for estimating the respiration condition of a subject, signal integration processing based on a Kalman filter is not implemented conventionally.

Related Art Literature

Patent Literature

Patent Literature 1: Japanese Patent Laid-Open No. 2015-83045

Non-Patent Literature

Non-Patent Literature 1: A. M. Chan, N. Ferdosi, and R. Narasimhan, "Ambulatory Respiratory Rate Detection using ECG and a Triaxial Accelerometer", 35th Annual International Conference of the IEEE EMBS, pp. 4058-4061, July, 2013

Non-Patent Literature 2: R. C. Luo, C. C. Yih, and K. L. Su, "Multisensor fusion and integration: approaches, applications, and future research directions", IEEE Journal Sensor, pp. 107-119, Vol. 2, no. 2, April 2002

Non-Patent Literature 3: Q Li, R G Mark, and G D Clifford, "Robust heart rate estimation from multiple asynchronous noisy sources using signal quality indices and a Kalman filter", Physiological Measurement, 29, pp. 15-32, 2008

DISCLOSURE OF INVENTION

Problem to be Solved by the Invention

The present invention has been made in consideration of the above problems, and has as its object to provide a respiration estimation method and apparatus capable of improving respiration estimation accuracy under various conditions.

Means of Solution to the Problem

According to the present invention, there is provided a respiration estimation method comprising a first step of estimating a breathing rate of a subject based on each of a time-series signal of first data related to a cardiac function of the subject and a time-series signal of second data relating to an acceleration by a respiratory motion of the subject, a second step of estimating a breathing rate obtained by filtering noise using a Kalman filter for each of the breathing rate estimated based on the first data and the breathing rate estimated based on the second data, and a third step of executing weighted averaging processing for the plurality of estimated values of the breathing rates obtained in the second step.

According to the present invention, there is also provided a respiration estimation apparatus comprising a breathing rate estimation unit configured to estimate a breathing rate of a subject based on each of a time-series signal of first data relating to a cardiac function of the subject and a time-series signal of second data relating to an acceleration by a respiratory motion of the subject, a Kalman filter configured to estimate a breathing rate obtained by filtering noise for each of the breathing rate estimated based on the first data and the breathing rate estimated based on the second data, and an integration processing unit configured to execute weighted averaging processing for the plurality of estimated values of the breathing rates obtained by the Kalman filter.

According to the present invention, there is also provided a respiration estimation method comprising a first step of extracting phase information from each of a time-series signal of first data relating to a cardiac function of a subject and a time-series signal of second data relating to an acceleration by a respiratory motion of the subject, a second step of estimating phase information obtained by filtering noise using a Kalman filter for each of the phase information of the first data and the phase information of the second data, a third step of executing weighted averaging processing for a plurality of estimated phase values obtained in the second step, and a fourth step of obtaining a respiration frequency of the subject by converting, into a frequency, a phase value integrated in the third step.

According to the present invention, there is also provided a respiration estimation apparatus comprising a feature amount extraction unit configured to extract phase information from each of a time-series signal of first data relating to a cardiac function of a subject and a time-series signal of second data relating to an acceleration by a respiratory motion of the subject, a Kalman filter configured to estimate phase information obtained by filtering noise for each of the phase information of the first data and the phase information of the second data, both of which have been obtained by the feature amount extraction unit, an integration processing unit configured to execute weighted averaging processing for an estimated phase value of the first data and an estimated phase value of the second data, both of which have been obtained by the Kalman filter, and a respiration frequency conversion unit configured to obtain a respiration frequency of the subject by converting, into a frequency, a phase value integrated by the integration processing unit.

Effect of the Invention

According to the present invention, by estimating the breathing rate of a subject based on each of the time-series signal of the first data relating to the cardiac function of the subject and the time-series signal of the second data relating to an acceleration by the respiratory motion of the subject, estimating, using a Kalman filter, a breathing rate obtained by filtering noise for each of the breathing rate estimated based on the first data and that estimated based on the second data, and performing weighted averaging processing for the plurality of estimated values of the breathing rates obtained by the Kalman filter, it is possible to estimate the breathing rate of the subject with respect to the individual difference or a wide variety of measurement conditions, and reduce the influence of an artifact of the body motion of the subject, thereby improving respiration estimation accuracy.

Furthermore, according to the present invention, by extracting phase information from each of the time-series signal of the first data relating to the cardiac function of a subject and the time-series signal of the second data relating to an acceleration by the respiratory motion of the subject, processing each piece of phase information by a Kalman filter, and performing weighted averaging processing for the estimated phase value of the first data and that of the second data, it is possible to estimate the respiration frequency of the subject with respect to the individual difference or a wide variety of measurement conditions, and reduce the influence of an artifact of the body motion of the subject, thereby improving respiration estimation accuracy.

BRIEF DESCRIPTION OF DRAWINGS

FIG. 9 is a block diagram showing the arrangement of a respiration estimation apparatus according to the second embodiment of the present invention;

FIG. 10 is a flowchart for explaining the operation of the respiration estimation apparatus according to the second embodiment of the present invention FIG. 11 is a flowchart for explaining, in detail, an operation after feature amount extraction processing according to the second embodiment of the present invention;

FIG. 13 is a flowchart for explaining a detailed operation of the feature amount extraction unit of the respiration estimation apparatus according to the second embodiment of the present invention;

FIG. 14 is a view for explaining processing by a Kalman filter of the respiration estimation apparatus according to the second embodiment of the present invention;

BEST MODE FOR CARRYING OUT THE INVENTION

First Embodiment

Figure 1:
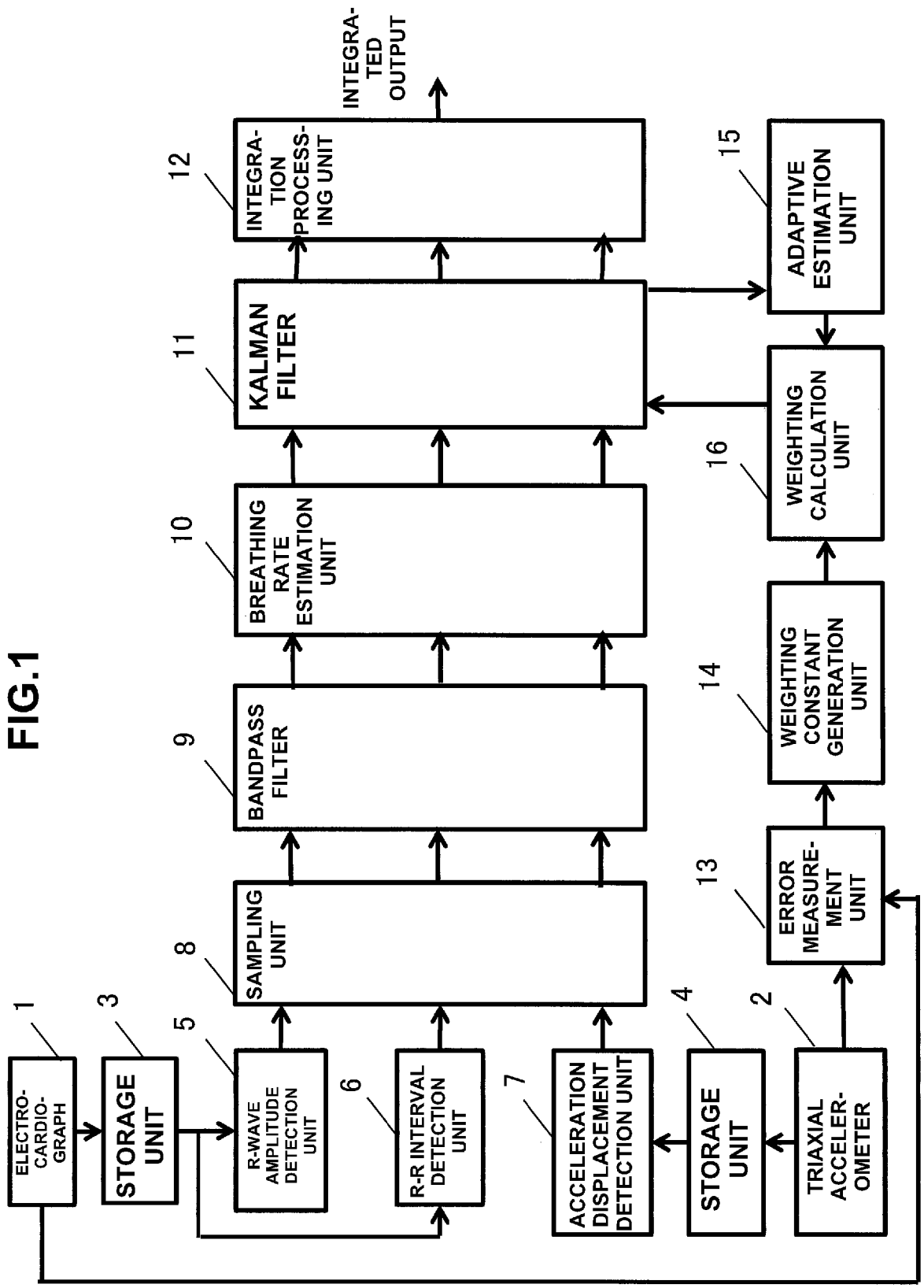
FIG. 1 is a block diagram showing an example of the arrangement of a respiration estimation apparatus according to the first embodiment of the present invention.

The embodiment of the present invention will be described below with reference to the accompanying drawings. FIG. 1 is a block diagram showing the arrangement of a respiration estimation apparatus according to the first embodiment of the present invention. The respiration estimation apparatus includes an electrocardiograph 1 for measuring the cardiac potential waveform of a subject, a triaxial accelerometer 2 for detecting a triaxial acceleration by the respiratory motion of the subject, storage units 3 and 4 for storing data obtained by the electrocardiograph 1 and the triaxial accelerometer 2, an R-wave amplitude detection unit 5 for detecting an R-wave amplitude from the cardiac potential waveform, an R-R interval detection unit 6 for detecting an R-R interval from the cardiac potential waveform, and an acceleration displacement detection unit 7 for detecting the angular displacement of an acceleration vector from a triaxial acceleration signal. The respiration estimation apparatus also includes a sampling unit 8 for sampling each of the time-series signal of the R-wave amplitude, that of the R-R interval, and that of the angular displacement, and a bandpass filter 9 for limiting the band of each of the time-series signal of the R-wave amplitude, that of the R-R interval, and that of the angular displacement. Furthermore, the respiration estimation apparatus includes a breathing rate estimation unit 10 for obtaining the frequency spectrum of each of the signals of the R-wave amplitude, the R-R interval, and the angular displacement by performing fast Fourier transform for each of the time-series signal of the R-wave amplitude, that of the R-R interval, and that of the angular displacement, all of which have been obtained by the bandpass filter 9, and estimating the breathing rate of the subject based on each of the frequency spectra. The respiration estimation apparatus includes a Kalman filter 11 for estimating the breathing rate obtained by filtering noise for each of the breathing rate estimated based on the time-series signal of the R-wave amplitude, that estimated based on the time-series signal of the R-R interval, and that estimated based on the time-series signal of the angular displacement, and an integration processing unit 12 for integrating data by performing weighted averaging for the estimated values of the breathing rates obtained by the Kalman filter 11. Furthermore, the respiration estimation apparatus includes an error measurement unit 13 for measuring error coefficients respectively indicating the reliabilities of the R-wave amplitude, R-R interval, and angular displacement, a weighting constant generation unit 14 for obtaining weighting constants as elements of a weighting matrix based on the error coefficients, an adaptive estimation unit 15 for updating the covariance estimation error matrix of the Kalman filter 11 so that an estimation error of the Kalman filter 11 becomes the minimum, and a weighting calculation unit 16 for updating a Kalman gain based on the weighting matrix and the covariance estimation error matrix.

Figure 2:
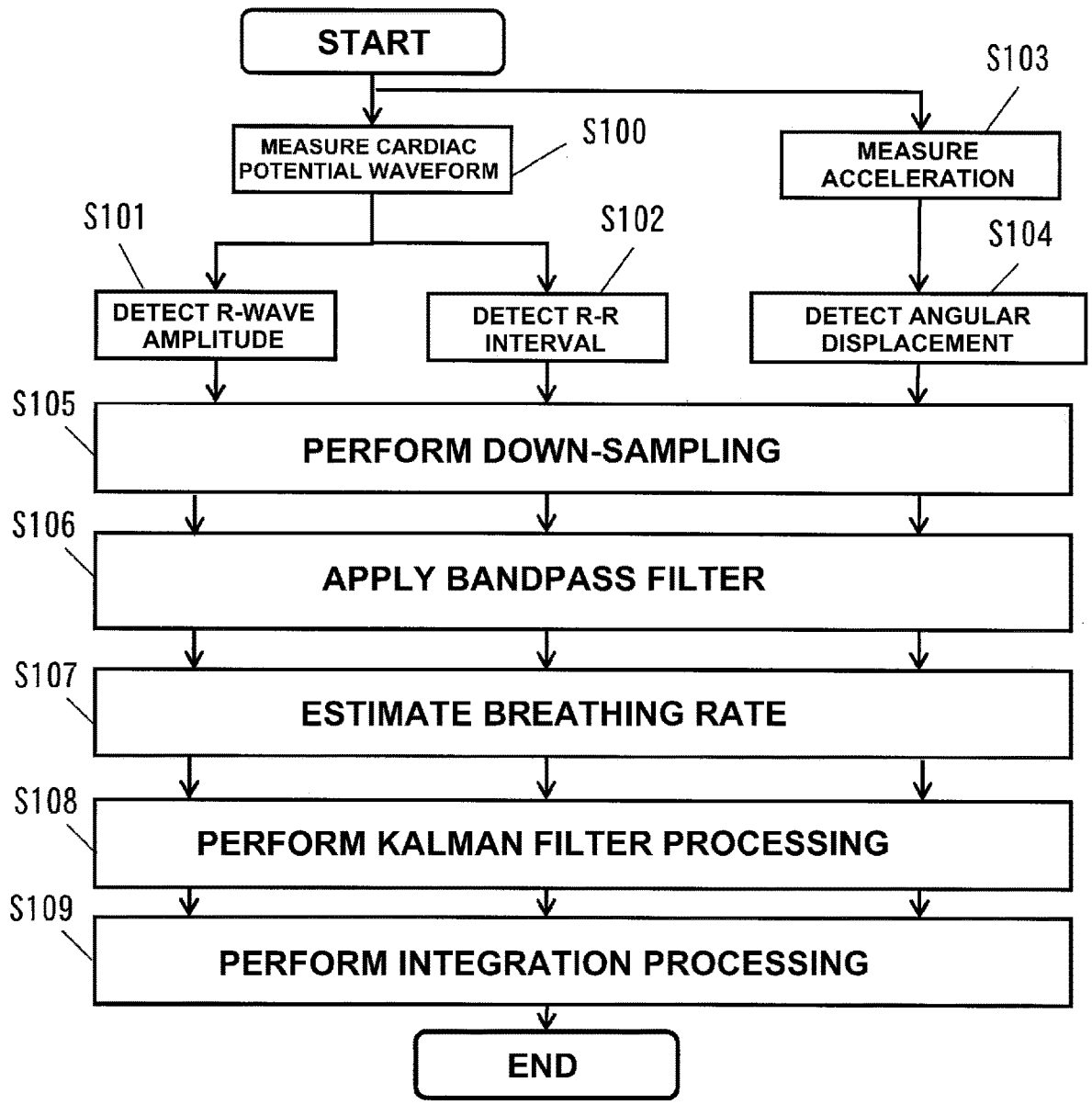
FIG. 2 is a flowchart for explaining the operation of the respiration estimation apparatus according to the first embodiment of the present invention.

FIG. 2 is a flowchart for explaining the operation of the respiration estimation apparatus. The electrocardiograph 1 measures the cardiac potential waveform of a subject, and outputs the time-series signal string of the cardiac potential waveform (step S100 of FIG. 2). The storage unit 3 stores the time-series signal string of the cardiac potential waveform output from the electrocardiograph 1.

As is well known, the cardiac potential waveform is formed from continuous heartbeat waveforms, and one heartbeat waveform is formed from components such as P, Q, R, S, and T waves reflecting the activities of atriums and ventricles. The R-wave amplitude detection unit 5 detects the amplitude of the R wave from the signals of the cardiac potential waveform stored in the storage unit 3 (step S101 of FIG. 2).

More specifically, the R-wave amplitude detection unit 5 detects the peaks of the R, Q, and S waves using wavelet transform. The R-wave amplitude detection unit 5 sets an amplitude from the peak value of the R wave to that of the S wave as the R-wave amplitude. It is possible to reduce the influence of the variation of the base line of the cardiac potential waveform using the difference between the R and S waves. The R-wave amplitude detection unit 5 detects an amplitude for each R wave of the cardiac potential waveform.

The R-R interval detection unit 6 detects an R-R interval from the signals of the cardiac potential waveform stored in the storage unit 3 (step S102 of FIG. 2). The R-R interval detection unit 6 detects the peak of the R wave using wavelet transform, as described above, and obtains an R-R interval as an interval between the R wave and the immediately preceding R wave. The R-R interval detection unit 6 detects an R-R interval for each R wave of the cardiac potential waveform.

On the other hand, the triaxial accelerometer 2 is mounted, for example, on the chest of the subject, and detects a triaxial acceleration by the respiratory motion of the subject and outputs the time-series signal string of the triaxial acceleration (step S103 of FIG. 2). The storage unit 4 stores the time-series signal string of the triaxial acceleration output from the triaxial accelerometer 2. Note that the triaxial accelerometer 2 according to this embodiment includes a rotation speed detection means, for example, a gyro sensor (not shown), and can detect a rotation speed with respect to each of three axes in the X, Y, and Z directions.

The acceleration displacement detection unit 7 detects the angular displacement of an acceleration vector from the signals of the triaxial acceleration stored in the storage unit 4 (step S104 of FIG. 2). To detect the angular displacement, after defining an acceleration change surface from the average of the acceleration displacements in three axial directions, that is, the X, Y, and Z directions, the angle of a projection vector obtained when an acceleration vector formed from the acceleration data of the three axes in the X, Y, and Z directions is projected on the change surface is calculated as the angular displacement.

This method is disclosed in, for example, A. Bates, M. J. Ling, J. Mann and D. K. Arvind, "Respiratory rate and flow waveform estimation from tri-axial accelerometer data", International Conference on Body Sensor Network, pp. 144-150, June 2010. The acceleration displacement detection unit 7 detects an angular displacement for each sampling period of the acceleration.

Subsequently, the sampling unit 8 down-samples each of the time-series signal of the R-wave amplitude output from the R-wave amplitude detection unit 5, the time-series signal of the R-R interval output from the R-R interval detection unit 6, and the time-series signal of the angular displacement output from the acceleration displacement detection unit 7 at a sampling frequency (for example, a 15-Hz interval) lower than the sampling frequency of the electrocardiograph 1 and that of the triaxial accelerometer 2 (step S105 of FIG. 2). Furthermore, the sampling unit 8 samples each of the time-series signal of the R-wave amplitude and that of the R-R interval in a time domain of 30 sec by a step size of 5 sec after down-sampling the signal at a 15-Hz interval. Note that the DC (Direct Current) component is deleted.

The bandpass filter 9 limits the band of each of the time-series signal of the R-wave amplitude, that of the R-R interval, and that of the angular displacement, all of which have been acquired by the sampling unit 8 (step S106 of FIG. 2). The reason why the bandpass filter 9 is used is that the respiration frequency of a person is limited to only a low frequency. The typical pass band of the bandpass filter 9 is, for example, 0.15 to 0.4 Hz.

Note that since the estimated values of the breathing rates obtained based on the time-series signal of the R-wave amplitude, that of the R-R interval, and that of the angular displacement are different from each other, a different value may be set as the pass band of the bandpass filter 9 with respect to each of the time-series signals. For example, the breathing rate obtained from the angular displacement is 6 to 60 BrPM (0.1 to 1.0 Hz), the breathing rate obtained from the R-wave amplitude is about 6 BrPM to half the heart rate, and the breathing rate obtained from the R-R interval is about 9 BrPM to half the heart rate.

Figure 3:
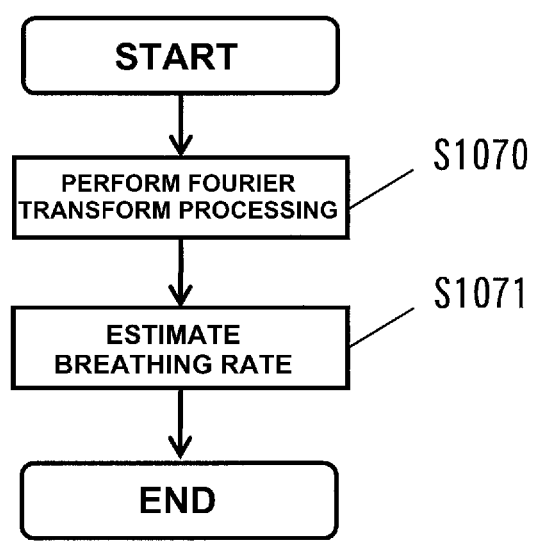
FIG. 3 is a flowchart for explaining a detailed operation of a breathing rate estimation unit of the respiration estimation apparatus according to the first embodiment of the present invention.

The breathing rate estimation unit 10 estimates the breathing rate of the subject based on each of the time-series signal of the R-wave amplitude, that of the R-R interval, and that of the angular displacement, whose band has been limited by the bandpass filter 9 (step S107 of FIG. 2). In this embodiment, it is assumed that when the respiratory motion of a person is represented by a waveform, the respiratory motion of a person is expressed by a sine wave in the ideal model of a pneumogram, and breathing rate information is extracted by frequency analysis. FIG. 3 is a flowchart for explaining a detailed operation of the breathing rate estimation unit 10.

After multiplying, by a Hamming window function, each of the time-series signal of the R-wave amplitude, that of the R-R interval, and that of the angular displacement, the breathing rate estimation unit 10 performs fast Fourier transform for each of the time-series signal of the R-wave amplitude, that of the R-R interval, and that of the angular displacement, thereby obtaining the frequency spectrum of each of the signals of the R-wave amplitude, the R-R interval, and the angular displacement (step S1070 of FIG. 3). As is well known, the Hamming window function is used to cut desired input data.

The breathing rate estimation unit 10 detects a peak frequency as the respiration frequency of the subject with respect to each of the frequency spectrum of the R-wave amplitude, that of the R-R interval, and that of the angular displacement, all of which have been obtained by fast Fourier transform.

At this time, if a plurality of peaks appear in the frequency spectrum, the breathing rate estimation unit 10 sets, as a respiration frequency obtained from the frequency spectrum, the frequency of the peak whose intensity is the maximum. The breathing rate is the reciprocal of the respiration frequency. Thus, the breathing rate estimation unit 10 can estimate the breathing rate of the subject from each of the time-series signal of the R-wave amplitude, that of the R-R interval, and that of the angular displacement (step S1071 of FIG. 3).

Next, the Kalman filter 11 estimates the breathing rate obtained by filtering noise for each of the breathing rate estimated by the breathing rate estimation unit 10 based on the time-series signal of the R-wave amplitude, the breathing rate estimated by the breathing rate estimation unit 10 based on the time-series signal of the R-R interval, and the breathing rate estimated by the breathing rate estimation unit 10 based on the time-series signal of the angular displacement (step S108 of FIG. 2).

Figure 4:
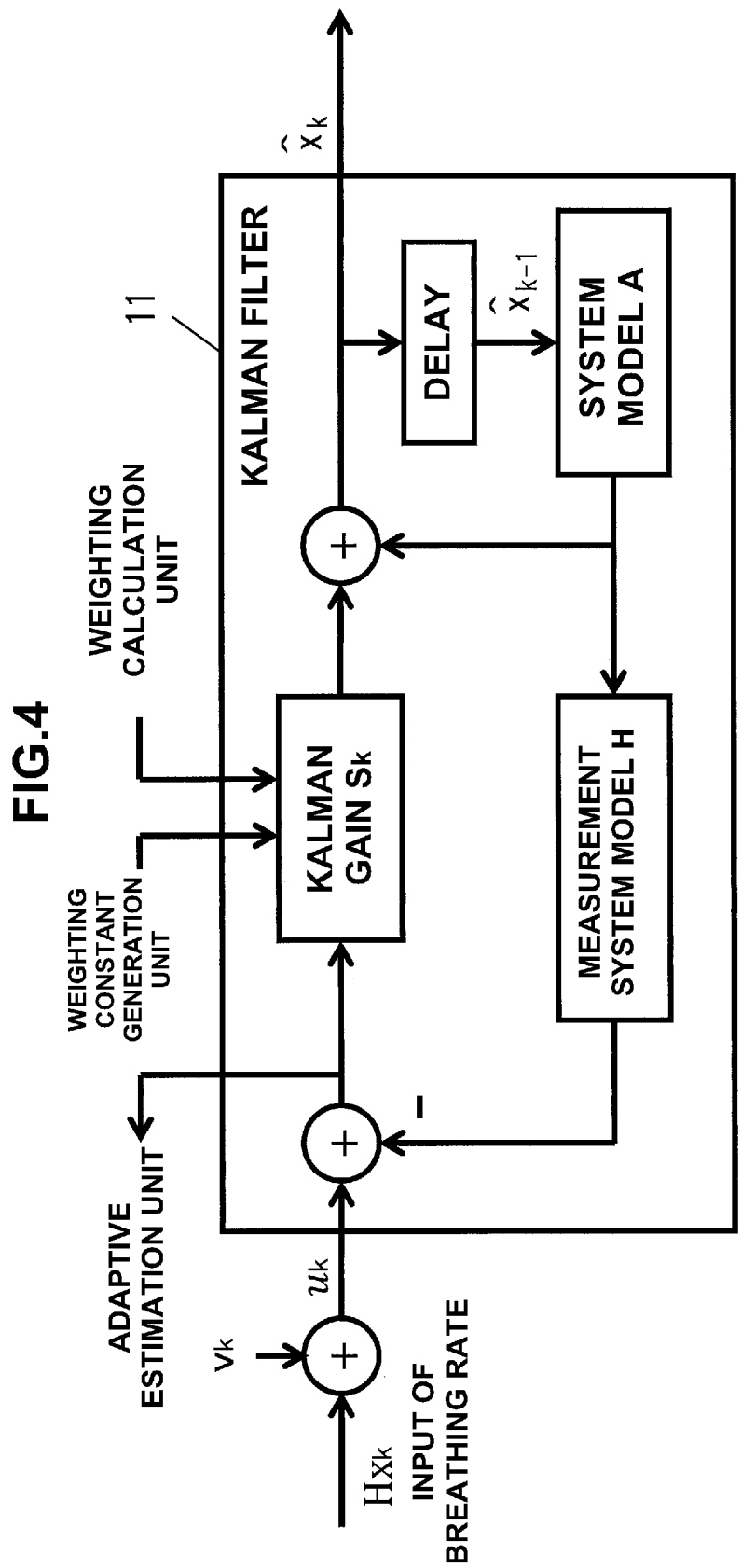
FIG. 4 is a block diagram showing a Kalman filter of the respiration estimation apparatus according to the first embodiment of the present invention.

FIG. 4 is a block diagram showing the arrangement of the Kalman filter 11. The Kalman filter based on Bayesian estimation and automatic recursive estimation is known as an optimal linear estimator when noise is uncorrelated, zero-mean, and white noise. Even if this condition is not true, the Kalman filter is considered as not an optimal linear estimator but a best linear estimator. The value of the breathing rate estimated by the breathing rate estimation unit 10 based on the time-series signal of the R-wave amplitude, the value of the breathing rate estimated by the breathing rate estimation unit 10 based on the time-series signal of the R-R interval, and the value of the breathing rate estimated by the breathing rate estimation unit 10 based on the time-series signal of the angular displacement are input to the Kalman filter 11. A physical quantity $x_k$ that describes a biological system is recursively determined, and given by the following equation.

$$x_{k+1} = Ax_k + w_k \quad (3)$$

$$u_k = Hx_k + v_k \quad (4)$$

Note that $u_k$ represents a system input, and $x_k$ represents a physical quantity without noise.

Furthermore, A represents an n×m matrix (m represents a measurement count and n represents the number of signals from the biological system, and n=3 in this embodiment) indicating a system model, and H is an m×n matrix indicating a measurement system model. As given by equation (3), the physical quantity $x_{k+1}$ includes the physical quantity $Ax_k$ at previous time and biological system noise of $w_k$. As given by equation (4), the system input $u_k$ includes the measured value $Hx_k$ and measurement system noise of $v_k$. In this embodiment, the measured value $Hx_k$ is the value of the breathing rate input from the breathing rate estimation unit 10. The system is updated by the following equations.

$$d_k = u_k - HA\hat{x}_{k-1} \quad (5)$$

$$\hat{x}_k = A\hat{x}_{k-1} + S_k d_k \quad (6)$$

Note that $d_k$ represents Kalman innovation, and $x_k$ represents the estimated value of the physical quantity $x_k$ (in this embodiment, the estimated value of the breathing rate). "^" above a letter will be referred to as "hat" hereinafter. $S_k$ is different from the Kalman gain of a conventional n×m matrix. The changed Kalman gain $S_k$ is given by the following equation.

$$S_k = P_k^- H^T (HP_k^- H^T + G_k)^{-1} \quad (7)$$

Note that $P_k^-$ represents the covariance estimation error matrix of $\hat{x}_k$, $H^T$ represents the transposed matrix of a matrix H, $G_k$ represents a parameter (matrix) based on $R_k$ as the covariance matrix of the measurement system noise $v_k$. According to equation (7), the parameter $G_k$ is obtained by adjusting the covariance matrix $R_k$ using known information, thereby determining the changed Kalman gain $S_k$. The known information is, for example, impulse noise from the outside or sensor-specific noise, and is formed by the stationary parameter and the constant from the weighting calculation unit 16.

The parameter $G_k$ includes information that cannot be used by the conventional Kalman filter, and is thus inappropriate to be used to update the covariance estimation error matrix $P_k^-$. A method of estimating the parameter $G_k$ will be described later. In this embodiment, a standard calculation method using the covariance matrix $R_k$ is adopted for update of the covariance estimation error matrix $P_k^-$. A conventional Kalman gain matrix $K_k$ is defined by the following equations.

$$K_k = P_k^- H^T (HP_k^- H^T + R_k)^{-1} \quad (8)$$

$$P_k^+ = (I - K_k H) P_k^- \quad (9)$$

$$P_{k+1}^- = A P_k^+ A^T + Q_k \quad (10)$$

Note that $P_k^+$ represents the covariance estimation error matrix of $A\hat{x}_k$, $Q_k$ represents the covariance matrix of the biological system noise $w_k$, I represents a unit matrix, and $A^T$ represents the transposed matrix of the matrix A. There are a plurality of methods of adaptively obtaining the covariance matrices $Q_k$ and $R_k$ to be used for equations (8) and (10). In this embodiment, the adaptive estimation unit 15 estimates the value of the covariance matrix $R_k$ using the following equation.

$$\hat{C}_k = \frac{1}{m} \sum_{i=0}^{m-1} (d_{k-i})(d_{k-i})^T \quad (11)$$

Note that m represents a window length used for estimation. In the method of equation (11), the Kalman innovation $d_k$ needs to be stationary in the window. This precondition is approximation in the non-stationary biological system. When the Kalman filter is optimal, the Kalman innovation $d_k$ is zero-mean and white noise. When the Kalman innovation $d_k$ is non-zero mean and colored, there is an example of attempting whitening by adjusting the covariance matrix $R_k$. At this time, in the stationary system, the optimal covariance matrix $R_k$ finally reaches a constant value. Since this embodiment is based on the non-stationary biological system, it is assumed that the biological system enters the stationary state at a limited window length m. In this embodiment, similar approximation is applied to another stationary parameter such as a Kalman gain.

With respect to the covariance matrix $Q_k$ of the biological system noise $w_k$, there is known an estimation method, similarly to the covariance matrix $R_k$. However, it is impossible to assume the stationary state, and it is thus considered that an error is included. To cope with this, in this embodiment, a predetermined matrix with an element artificially preset to a large value is set as the covariance matrix $Q_k$, and the assumption that an error of the model is large is posed, thereby making the reliability of a new estimated value higher than that of an old estimated value.

The weighting constant generation unit 14 will be described next. As described above, it is necessary to input the known information to the Kalman filter 11. In this embodiment, weighting constants as elements of the weighting matrix $W_k$ are obtained by measuring errors of the signals obtained from the electrocardiograph 1 and the triaxial accelerometer 2. Each weighting constant is fed back to the system in accordance with the reliability of the information.

Each constant (error coefficient) to be fed back is determined within the range of −1 to +1. When the reliability of the information is low, the error coefficient is set to −1. When the reliability of the information is high, the error coefficient is set to +1. When an error is unknown, the error coefficient is set to 0. A practical method of determining the error coefficients by the error measurement unit 13 will be described later.

The error coefficients are arranged as diagonal elements of the weighting matrix $W_k$ relating to a Kalman filter state. For example, the error coefficient of the acceleration is arranged as a diagonal element $W_{11}$ of the weighting matrix $W_k$, the error coefficient of the R-R interval is arranged as a diagonal element $W_{22}$ of the weighting matrix $W_k$, and the error coefficient of the R-wave amplitude is arranged as a diagonal element $W_{33}$ of the weighting matrix $W_k$.

In this embodiment, a weighting covariance between the signals is also necessary. When the two signals have small errors or large errors, the similar error coefficients are obtained but do not mean that the two signals depend on each other. However, variations of the errors of the signals must be associated with independent noise sources.

In this embodiment, using the difference between the error coefficients, the weighting constants arranged as non-diagonal elements $W_{ij}$ and (i and j are indices each indicating the dimension of the weighting constant W, and i≠j) of the weighting matrix $W_k$ are calculated by the following equation.

$$W_{ij}=W_{ji}=-|W_{ii}-W_{jj}|/2 \quad (12)$$

Note that k representing a time index is not described in equation (12). In this way, the weighting constant generation unit 14 determines the weighting matrix $W_k$ based on the error coefficients output from the error measurement unit 13.

To obtain the parameter $G_k$ used for equation (7), the weighting matrix $W_k$ is simply used to calculate equation (13) below.

$$G_k=(1+\alpha W_k) \circ R_k \quad (13)$$

A symbol "∘" in equation (13) represents an Hadamard product. α represents a scale factor for adjusting the intensity of each error coefficient (0≤α≤1). To improve the convergence, α is set to, for example, 0.5.

Figure 5:
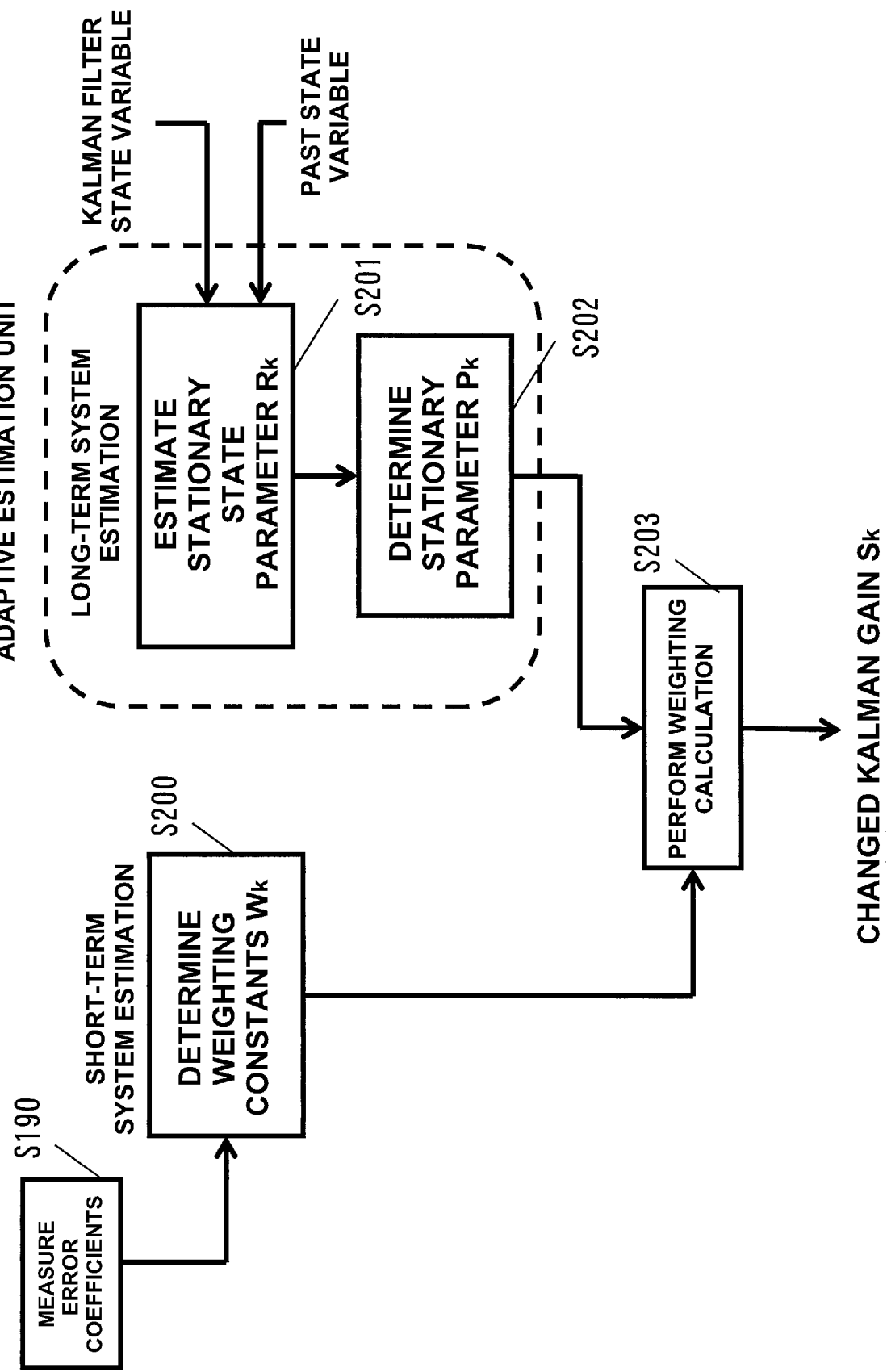
FIG. 5 is a flowchart for explaining the operations of a weighting constant generation unit, weighting calculation unit, and adaptive estimation unit of the respiration estimation apparatus according to the first embodiment of the present invention.

FIG. 5 is a flowchart for explaining the operations of the weighting constant generation unit 14, adaptive estimation unit 15, and weighting calculation unit 16. As described above, based on the error coefficients obtained by error measurement at the given window length m (measurement count), the weighting constant generation unit 14 performs short-term system estimation to determine the weighting matrix $W_k$ (step S200 of FIG. 5).

The adaptive estimation unit 15 assumes an ideal noise state (the Kalman innovation is in the stationary state) from the Kalman filter state and the past state, estimates the covariance matrix $R_k$ by performing long-term system estimation by a known method (step S201 of FIG. 5), and determines the covariance estimation error matrix $P_k^-$ as the stationary parameter by equations (8) to (10) (step S202 of FIG. 5). Equations (8) to (10) represent a well-known method of recursively determining the Kalman gain $K_k$ so that the estimation error of $\hat{x}_k$ becomes minimum. It is possible to update the covariance estimation error matrices $P_k^-$ and $P_k^+$ by this method.

The weighting calculation unit 16 calculates the parameter $G_k$ by equation (13) using the weighting matrix $W_k$ determined by the weighting constant generation unit 14, and calculates the changed Kalman gain $S_k$ by equation (7) using the parameter $G_k$ and the covariance estimation error matrix $P_k^-$ determined by the adaptive estimation unit 15 (step S203 of FIG. 5). Thus, the Kalman gain $S_k$ can be adaptively changed.

In this embodiment, the system is defined the following equations.

$$x=[x_{acc} x_{RRI} x_{RA}]^T \quad (14)$$

$$u=[u_{acc} u_{RRI} u_{RA}]^T \quad (15)$$

In equation (14), $X_{acc}$ represents the breathing rate estimated by the breathing rate estimation unit 10 based on the time-series signal of the angular displacement (triaxial acceleration), RRI represents the breathing rate estimated by the breathing rate estimation unit 10 based on the time-series signal of the R-R interval, and $x_{RA}$ represents the breathing rate estimated by the breathing rate estimation unit 10 based on the time-series signal of the R-wave amplitude. $u_{acc}$, $U_{RRI}$, and $u_{RA}$ are system inputs corresponding to $x_{acc}$, $x_{RRI}$, and $x_{RA}$, respectively.

This embodiment has as its feature to integrate the breathing rate estimated based on the time-series signal of the R-wave amplitude, that estimated based on the time-series signal of the R-R interval, and that estimated based on the time-series signal of the angular displacement (triaxial acceleration). That is, based on the parameter $G_k$, the changed Kalman gain $S_k$, and the matrix A given by equation (16), the three estimated values of the breathing rates are integrated into one estimated value by equation (6).

$$A = \begin{bmatrix} 1 & 0 & 0 \\ 1 & 0 & 0 \\ 1 & 0 & 0 \end{bmatrix} \quad (16)$$

Note that the measurement system model can be expressed by the following equation.

$$H = \begin{bmatrix} 1 & 0 & 0 \\ 0 & 1 & 0 \\ 0 & 0 & 1 \end{bmatrix} \quad (17)$$

In this embodiment, as described above, since the covariance matrix $R_k$ is estimated by the adaptive estimation unit 15 and the covariance matrix $Q_k$ is set to have fixed values without estimating it, it is necessary to determine the covariance matrix $Q_k$ in advance. To simplify the system, it is assumed that process noise is independent. That is, the covariance matrix $Q_k$ is determined so that only the diagonal elements have values and the non-diagonal elements have 0.

For example, an element corresponding to the acceleration is arranged as a diagonal element $Q_{11}$ of the covariance matrix $Q_k$, an element corresponding to the R-R interval is arranged as a diagonal element $Q_{22}$ of the covariance matrix $Q_k$, and an element corresponding to the R-wave amplitude is arranged as a diagonal element $Q_{33}$ of the covariance matrix $Q_k$. The values of the diagonal elements have the same value for the respective signals (acceleration, R-wave amplitude, and R-R interval).

Based on the matrix A of equation (16), the three estimated values of the breathing rates are integrated into one estimated value by equation (6). When the matrix A is given by equation (18), the integration processing unit 12 integrates the estimated values of the breathing rates.

$$A = \begin{bmatrix} 1 & 0 & 0 \\ 0 & 1 & 0 \\ 0 & 0 & 1 \end{bmatrix} \quad (18)$$

The integration processing unit 12 performs, using weights based on the squared estimation errors of the Kalman filter 11, weighted averaging processing for the estimated value of the breathing rate based on the time-series signal of the R-wave amplitude, that based on the time-series signal of the R-R interval, and that based on the time-series signal of the angular displacement (triaxial acceleration), thereby integrating the estimated values of the breathing rates (step S109 of FIG. 2).

Figure 6:
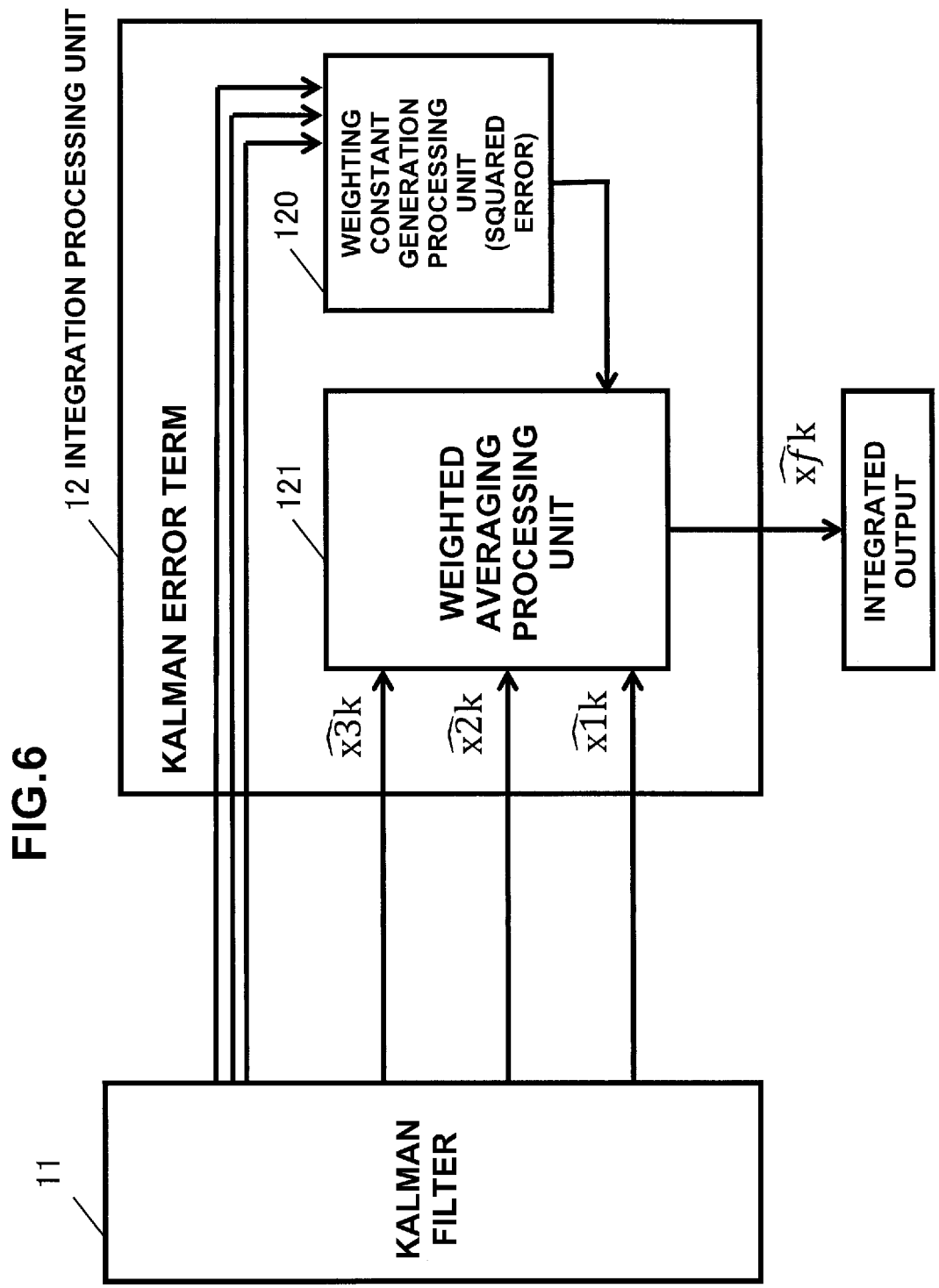
FIG. 6 is a block diagram showing an example of the arrangement of an integration processing unit of the respiration estimation apparatus according to the first embodiment of the present invention.
Figure 7:
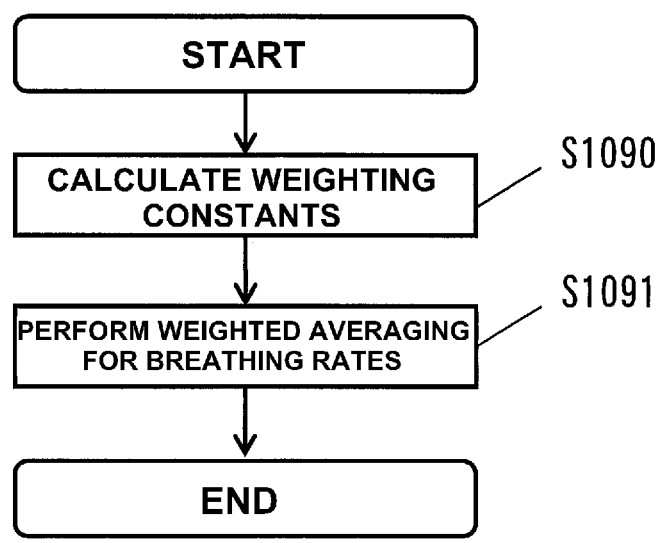
FIG. 7 is a flowchart for explaining a detailed operation of the integration processing unit of the respiration estimation apparatus according to the first embodiment of the present invention.

FIG. 6 is a block diagram showing the arrangement of the integration processing unit 12. FIG. 7 is a flowchart for explaining a detailed operation of the integration processing unit 12. The integration processing unit 12 includes a weighting constant generation processing unit 120 for calculating a weighting constant for integration processing from the squared estimation error of the Kalman filter 11 with respect to each of the breathing rate based on the time-series signal of the R-wave amplitude, that based on the time-series signal of the R-R interval, and that based on the time-series signal of the angular displacement (triaxial acceleration), and a weighted averaging processing unit 121 for performing weighted averaging for the plurality of estimation values of the breathing rates using the weighting constants. In the above-described Kalman filter processing, the estimated value of the breathing rate is obtained at each time while the changed Kalman gain $S_k$ and the covariance estimation error matrices $P_k^-$ and $P_k^+$ are updated.

The squared estimation errors of the Kalman filter 11 can be obtained from the covariance estimation error matrix $P_k^+$. In this embodiment, σ1 of represents the squared estimation error of the breathing rate based on the time-series signal of the angular displacement (triaxial acceleration), σ2 represents the squared estimation error of the breathing rate based on the time-series signal of the R-R interval, and σ3 represents the squared estimation error of the breathing rate based on the time-series signal of the R-wave amplitude.

The weighting constant generation processing unit 120 calculates a weighting constant αi from the squared estimation error σi of each of the R-wave amplitude, R-R interval, and angular displacement by equation (19) below (step S1090 of FIG. 7).

$$\alpha i = \frac{1/\sigma i^2}{1/\sigma 1^2 + 1/\sigma 2^2 + 1/\sigma 3^2} \quad (19)$$

The weighting constant generation processing unit 120 performs calculation by equation (19) for each of the R-wave amplitude, R-R interval, and angular displacement. Using the weighting constants αi (i=1, 2, 3) calculated by the weighting constant generation processing unit 120, the weighted averaging processing unit 121 calculates an integrated output value $\hat{x}f_k$ as the value of the breathing rate obtained by performing weighted averaging processing for an estimated value $\hat{x}1$ of the breathing rate based on the time-series signal of the angular displacement (triaxial acceleration), an estimated value $\hat{x}2$ of the breathing rate based on the time-series signal of the R-R interval, and an estimated value 23 of the breathing rate based on the time-series signal of the R-wave amplitude, as given by equation (20) (step S1091 of FIG. 7). The integration processing unit 12 performs the above integration processing at each time.

$$\hat{x}f_k = \frac{\sum_i \alpha i \hat{x}i}{\alpha 1 + \alpha 2 + \alpha 3} \quad (20)$$

A method of determining error coefficients by the error measurement unit 13 will be described next. With respect to the error coefficient of the acceleration, the gyro sensor of the triaxial accelerometer 2 detects the rotation speed for each of the three axes in the X, Y, and Z directions. The error measurement unit 13 sets the error coefficient of the acceleration to +1 when all of the rotation speeds for the three axes in the X, Y, and Z directions are equal to or higher than a predetermined first rotation speed threshold (for example, 0.2 rad/sec), and sets the error coefficient of the acceleration to −1 when all of the rotation speeds are equal to or lower than a predetermined second rotation speed threshold (for example, 0.003 rad/sec) (step S190 of FIG. 5).

When the representative value (for example, the average value) of the rotation speeds for the three axes in the X, Y, and Z directions falls between the first rotation speed threshold and the second rotation speed threshold, the error measurement unit 13 determines the error coefficient of the acceleration by a linear scaling method of assigning a value falling within the range of −1 to +1 in accordance with the representative value (step S190).

With respect to the error coefficient of the R-wave amplitude, the error measurement unit 13 extracts an error in accordance with each beat (step S190). More specifically, the error measurement unit 13 excludes the Q, R, and S waves from the cardiac potential waveform measured by the electrocardiograph 1, and calculates a correlation coefficient between the beats for the thus obtained waveform. The error measurement unit 13 sets the error coefficient of the R-wave amplitude to −1 when the correlation coefficient is a value equal to or larger than a predetermined correlation coefficient threshold, and sets the error coefficient of the R-wave amplitude to +1 when the correlation coefficient is equal to or smaller than 0. A large correlation coefficient indicates that noise from a noise source is large and an error is large.

When the calculated correlation coefficient falls between the predetermined correlation coefficient threshold and 0, the error measurement unit 13 determines the error coefficient of the R-wave amplitude by the linear scaling method of assigning a value falling within the range of −1 to +1 in accordance with the correlation coefficient.

On the other hand, there is no appropriate method of calculating an error coefficient for the R-R interval, and it is difficult to obtain an appropriate error coefficient. Therefore, the error measurement unit 13 sets the error coefficient of the R-R interval to a fixed value, more specifically, 0 (step S190).

Table 1 shows an RMS error (BrPM) of the data reconstruction result (breathing rate) by the respiration estimation apparatus according to this embodiment.

TABLE 1

| | Laying down | Sitting | Walking | Running |
|---|---|---|---|---|
| | Root-mean-square-error (BrPM) | | | |
| Acceleration ($u_{acc}$) | 5.73 | 5.93 | 16.6 | 11.5 |
| R-R interval ($u_{RRI}$) | 3.22 | 2.78 | 6.57 | 7.96 |
| R-wave amplitude ($u_{RA}$) | 2.43 | 2.57 | 9.94 | 11.0 |
| Integrated output ($\hat{x}_{acc}$) | 2.11 | 2.30 | 5.97 | 5.98 |

Table 1 shows comparison of an error of the breathing rate estimated based on the acceleration (angular displacement), an error of the breathing rate estimated based on the R-R interval, an error of the breathing rate estimated based on the R-wave amplitude, and an error of the integrated breathing rate (an integrated output from the integration processing unit 12) among the different orientations and actions of the subject. Table 1 shows errors of the estimated breathing rates for cases of laying down, sitting, walking, and running.

According to Table 1, the accuracy of the integrated output is better than that of the estimated value of the breathing rate estimated based on each of the acceleration, R-R interval, and R-wave amplitude. Furthermore, it is found that even in an action such as walking or running in which there is a large artifact, the error of the integrated output is small and the estimation accuracy is improved.

Figure 8:
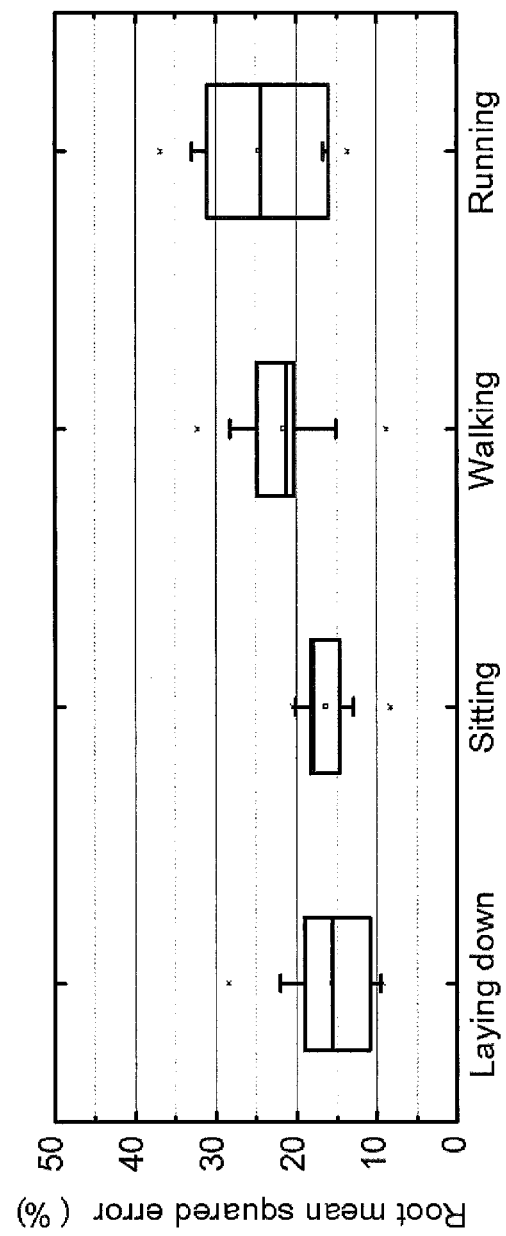
FIG. 8 is a view showing a breathing rate integration result by the respiration estimation apparatus according to the first embodiment of the present invention.

FIG. 8 shows estimation error rates for different individual differences in the integrated outputs from the integration processing unit 12 by a percentile graph for the cases of laying down, sitting, walking, and running. Referring to FIG. 8, it is found that even if the breathing rates are estimated for a plurality of subjects who are walking, an error rate of 30% or less can be achieved.

This embodiment estimates the breathing rate of the subject by integrating a plurality of sensor data and extracting the best data while adaptively changing the Kalman gain in order to cope with the individual difference of the age, autonomic nervous system, skin condition, and body structure of the subject.

When data of the triaxial acceleration is used to estimate the breathing rate, it is difficult to optimize the calculation equation due to the individual difference of the body motion or body structure of the subject. When data of the R-R interval is used to estimate the breathing rate, there is restriction on calculation of a respiration cycle by the cardiac cycle, and it is thus difficult to optimize the calculation equation due to the influence of the autonomic nervous system that changes depending on the mental condition and age of the subject. When data of the R-wave amplitude is used to estimate the breathing rate, it is difficult to optimize the calculation equation due to the individual difference of the skin condition, a change in contact impedance in accordance with the body motion or skin condition of the subject, or the like. Conversely, in this embodiment, even if the S/N ratio of the signal degrades, it is possible to reduce noise of the breathing rate and stably estimate the breathing rate by adaptively integrating the plurality of sensor data. Furthermore, in this embodiment, it is possible to reflect data relating to the cardiac function and the reliability of the acceleration data on the Kalman gain of the Kalman filter by providing the error measurement unit 13, weighting constant generation unit 14, adaptive estimation unit 15, and weighting calculation unit 16, thereby improving the estimation accuracy of the breathing rate.

The storage units 3 and 4, R-wave amplitude detection unit 5, R-R interval detection unit 6, acceleration displacement detection unit 7, sampling unit 8, bandpass filter 9, Kalman filter 11, integration processing unit 12, error measurement unit 13, weighting constant generation unit 14, adaptive estimation unit 15, and weighting calculation unit 16, all of which have been described in this embodiment, can be implemented by a computer including a CPU (Central Processing Unit), a storage device, and an interface, and a program for controlling these hardware resources. The CPU executes the processing described in this embodiment in accordance with programs stored in the storage device.

Note that the electrocardiograph 1 includes an electrode attached to clothing such as a shirt, and a cardiac potential waveform signal processing unit in a monitoring apparatus attached to the clothing, and the electrode and the cardiac potential waveform signal processing unit are connected by a wiring line. Similarly, the triaxial accelerometer 2 includes a sensor unit attached to the clothing and an acceleration signal processing unit provided in the monitoring apparatus, and the sensor unit and the acceleration signal processing unit are connected by a wiring line.

In this embodiment, the electrocardiograph 1 and the triaxial accelerometer 2 may be provided together with or separately from the wearable device attached to the clothing. That is, the storage units 3 and 4, R-wave amplitude detection unit 5, R-R interval detection unit 6, acceleration displacement detection unit 7, sampling unit 8, bandpass filter 9, Kalman filter 11, integration processing unit 12, error measurement unit 13, weighting constant generation unit 14, adaptive estimation unit 15, and weighting calculation unit 16 may be provided in the monitoring apparatus or provided in another apparatus.

When the storage units 3 and 4, R-wave amplitude detection unit 5, R-R interval detection unit 6, acceleration displacement detection unit 7, sampling unit 8, bandpass filter 9, Kalman filter 11, integration processing unit 12, error measurement unit 13, weighting constant generation unit 14, adaptive estimation unit 15, and weighting calculation unit 16 are provided in another apparatus, a cardiac potential waveform signal obtained by the electrocardiograph 1 and information of a triaxial acceleration signal and rotation speed signal obtained by the triaxial accelerometer 2 are wirelessly transmitted to the apparatus.

Second Embodiment

The second embodiment of the present invention will be described next. FIG. 9 is a block diagram showing the arrangement of a respiration estimation apparatus according to the second embodiment of the present invention. The respiration estimation apparatus includes an electrocardiograph 21, a triaxial accelerometer 22, storage units 23 and 24, an R-wave amplitude detection unit 25, an R-R interval detection unit 26, and an acceleration displacement detection unit 27. The respiration estimation apparatus also includes a sampling unit 28, a bandpass filter 29, and a feature amount extraction unit 30 for extracting phase information from each of the time-series signal of an R-wave amplitude, that of an R-R interval, and that of an angular displacement, all of which have been obtained by the bandpass filter 29. Furthermore, the respiration estimation apparatus includes a Kalman filter 31 for estimating phase information obtained by filtering noise for each of the phase information of the R-wave amplitude, that of the R-R interval, and that of the angular displacement, an integration processing unit 32 for integrating data by performing weighted averaging for the estimated phase value of the R-wave amplitude, that of the R-R interval, and that of the angular displacement, all of which have been obtained by the Kalman filter 31, and a respiration frequency conversion unit 33 for setting, as the respiration frequency of a subject, a result of converting the phase value integrated by the integration processing unit 32 into a frequency.

FIG. 10 is a flowchart for explaining the operation of the respiration estimation apparatus. The electrocardiograph 21 measures the cardiac potential waveform of a subject, and outputs the time-series signal string of the cardiac potential waveform (step S300 of FIG. 10). The storage unit 23 stores the time-series signal string of the cardiac potential waveform output from the electrocardiograph 21.

The R-wave amplitude detection unit 25 detects the amplitude of the R wave from the signals of the cardiac potential waveform stored in the storage unit 23 (step S301 of FIG. 10). As a method of recognizing the R wave of the cardiac potential waveform, there is provided, for example, a technique disclosed in Japanese Patent Laid-Open No. 2003-561. This technique recognizes an R wave using a threshold based on an amplitude between the peak and valley of the cardiac potential waveform. The R-wave amplitude detection unit 25 detects an amplitude for each R wave of the cardiac potential waveform.

The R-R interval detection unit 26 detects an R-R interval from the signals of the cardiac potential waveform stored in the storage unit 23 (step S302 of FIG. 10). As a technique of detecting the R-R interval of the cardiac potential waveform, for example, there is provided a technique disclosed in "ECG Implementation on the TMS320C5515 DSP Medical Development Kit (MDK) with the ADS1298 ECG-FE", Texas Instruments Incorporated, <http://www.ti.com/lit/an/sprabjl/sprabjl.pdf>, 2011. This technique obtains an R-R interval based on a change in value of the time difference of the cardiac potential waveform. The R-R interval detection unit 26 detects an R-R interval for each R wave of the cardiac potential waveform.

On the other hand, the triaxial accelerometer 22 is mounted on the chest of the subject, and detects a triaxial acceleration by the respiratory motion of the subject and outputs the time-series signal string of the triaxial acceleration (step S303 of FIG. 10). The storage unit 24 stores the time-series signal string of the triaxial acceleration output from the triaxial accelerometer 22.

Similarly to the acceleration displacement detection unit 7, the acceleration displacement detection unit 27 detects the angular displacement of an acceleration vector from the signals of the triaxial acceleration stored in the storage unit 24 (step S304 of FIG. 10). The acceleration displacement detection unit 27 detects an angular displacement for each sampling period of the acceleration.

Subsequently, the sampling unit 28 samples each of the time-series signal of the R-wave amplitude output from the R-wave amplitude detection unit 25, the time-series signal of the R-R interval output from the R-R interval detection unit 26, and the time-series signal of the angular displacement output from the acceleration displacement detection unit 27 at a sampling frequency (for example, a 1-Hz interval) lower than the sampling frequency of the electrocardiograph 21 and that of the triaxial accelerometer 22 (step S305 of FIG. 10).

The bandpass filter 29 limits the band of each of the time-series signal of the R-wave amplitude, that of the R-R interval, and that of the angular displacement, all of which have been acquired by the sampling unit 28 (step S306 of FIG. 10). The reason why the bandpass filter 29 is used is that the respiration frequency of a person is limited to only a low frequency. The pass band of the bandpass filter 29 is, for example, 0.15 to 0.4 Hz.

The procedure of the processing of the respiration estimation apparatus, that is related to the feature amount extraction unit 30, will be described in more detail with reference to a flowchart shown in FIG. 11. The feature amount extraction unit 30 extracts instantaneous linearized phase information, instantaneous amplitude information, and instantaneous frequency information from each of the time-series signal of the R-wave amplitude, that of the R-R interval, and that of the angular displacement, all of which have been obtained by the bandpass filter 29 (step S307 of FIGS. 10 and 11). In this embodiment, it is assumed that when the respiratory motion of a person is represented by a waveform, a change in breathing rate within a short time is negligibly small and the respiratory motion is expressed by a sine wave in the ideal model of a pneumogram, thereby extracting instantaneous phase information by Hilbert transform.

Figure 12A:
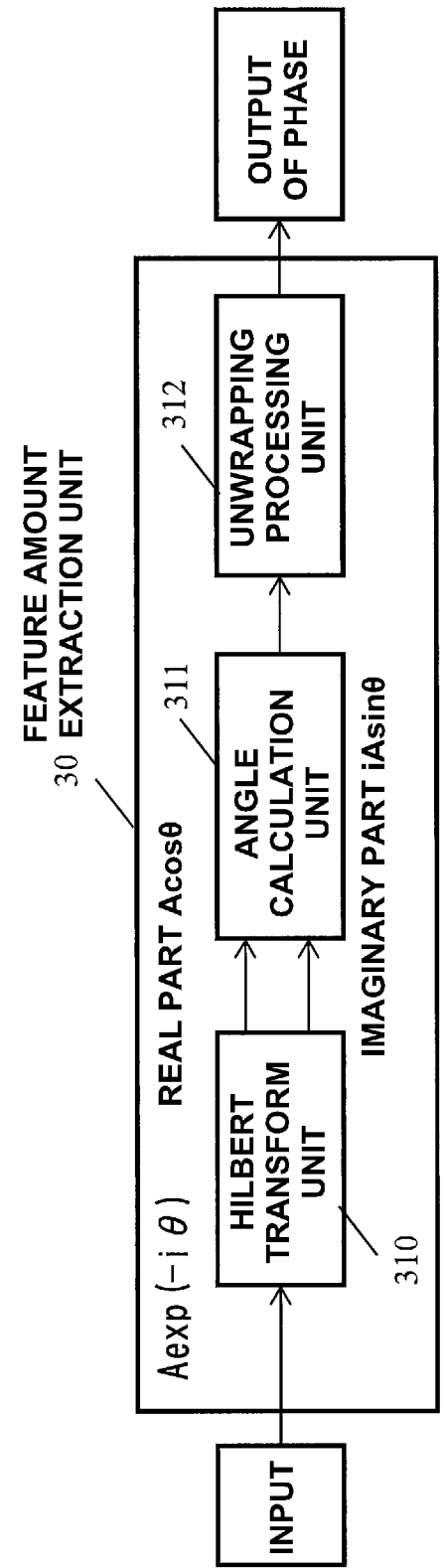
FIG. 12A is a block diagram showing the arrangement of a feather amount extraction unit of the respiration estimation apparatus according to the second embodiment of the present invention.

FIG. 12A is a block diagram showing the arrangement of the feature amount extraction unit 30. FIG. 13 is a flowchart for explaining a detailed operation of the feature amount extraction unit 30. The feature amount extraction unit 30 includes a Hilbert transform unit 310, an angle calculation unit 311, and an unwrapping processing unit 312.

Figure 12B:
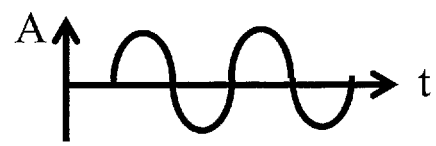
FIGS. 12B, 12C, and 12D are views showing the signal waveforms of the respective units of the feature amount extraction unit.

The Hilbert transform unit 310 Hilbert-transforms the time-series signal of the R-wave amplitude, that of the R-R interval, and that of the angular displacement, whose bands have been limited by the bandpass filter 29, thereby generating two signal components (real-part component and imaginary-part component) with phases different from each other by $\pi/2$ (step S3070 of FIG. 13). When a signal input to the Hilbert transform unit 310 is expressed by a sine wave of $A\exp(-i\theta)$ (FIG. 12B), the generated real-part component is a sine wave expressed by $A \cos \theta$, and the generated imaginary-part component is a signal of a sine wave expressed by $iA \sin \theta$ where A represents an amplitude, $\theta$ represents an angle, and i represents an imaginary unit.

Subsequently, the angle calculation unit 311 calculates the angle $\theta$ ($-\pi$ to $+\pi$) from the real-part component $A \cos \theta$ and the imaginary-part component $iA \sin \theta$ both of which have been generated by the Hilbert transform unit 310 (step S3071 of FIG. 13).

Figure 12C:
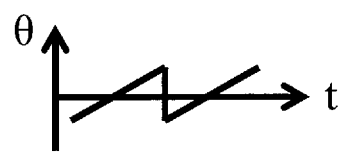
Figure 12D:
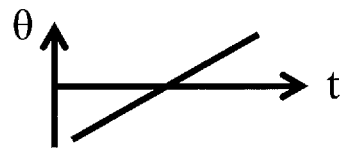

Finally, the unwrapping processing unit 312 performs phase unwrapping for linearizing the angle $\theta$ calculated by the angle calculation unit 311 to continuous phase values (step S3072 of FIG. 13). Since the angle $\theta$ calculated by the angle calculation unit 311 has a value between $-\pi$ and $+\pi$, a $2\pi$ phase jump may occur between adjacent points, as shown in FIG. 12C. The unwrapping processing unit 312 connects the phases by, for example, adding or subtracting $2\pi$. This obtains the continuous phase shown in FIG. 12D.

The feature amount extraction unit 30 performs the above processing for each of the time-series signal of the R-wave amplitude, that of the R-R interval, and that of the angular displacement, whose band has been limited by the bandpass filter 29. That is, three sets of Hilbert transform units 310, angle calculation units 311, and unwrapping processing units 312 are provided to simultaneously perform processes of the three time-series signals of the R-wave amplitude, R-R interval, and angular displacement.

Next, the Kalman filter 31 estimates phase information obtained by filtering noise for each of the phase information of the R-wave amplitude, that of the R-R interval, and that of the angular displacement (step S308 of FIGS. 10 and 11). As shown in FIG. 14, the Kalman filter 31 is provided for each of the R-wave amplitude, R-R interval, and angular displacement. The phase information of the R-wave amplitude, that of the R-R interval, and that of the angular displacement, all of which have been obtained by the feature amount extraction unit 30 are respectively input to corresponding Kalman filters 31-1, 31-2, and 31-3.

Figure 15:
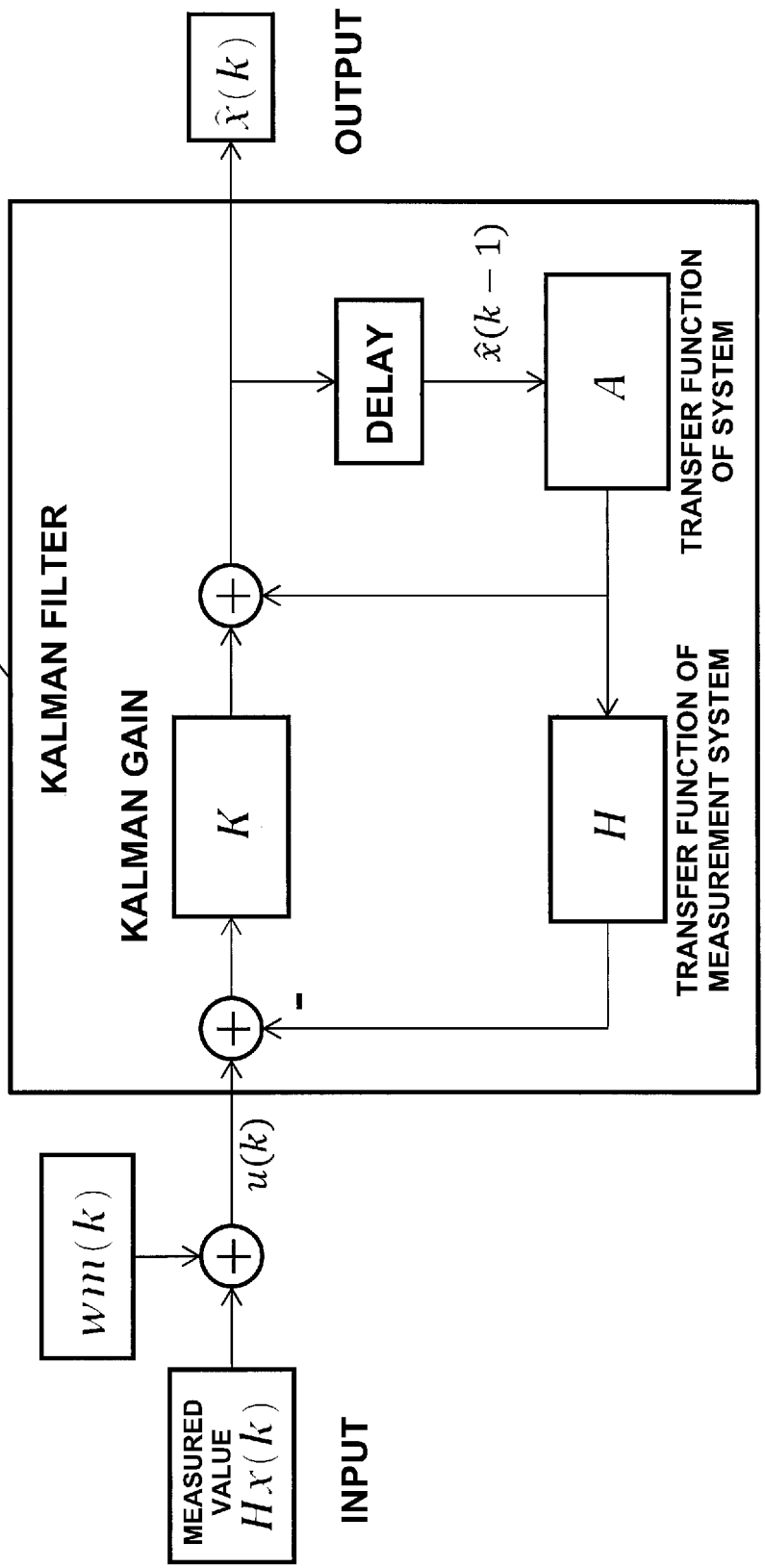
FIG. 15 is a block diagram showing the Kalman filter of the respiration estimation apparatus according to the second embodiment of the present invention.

FIG. 15 is a block diagram showing the Kalman filter 31. Note that the block diagram shows one of the three Kalman filters 31-1, 31-2, and 31-3. The Kalman filter is based on Bayesian estimation and automatic recursive estimation. Under the assumption that an input to a system includes Gaussian noise, a Kalman gain K is obtained by least squares approximation. A physical quantity x(k) that describes a biological system is recursively determined, and given by the following equation.

$$x(k+1)=Ax(k)+w_s(k) \qquad (21)$$

$$u(k)=Hx(k)+w_m(k) \qquad (22)$$

Note that u(k) represents a system input, and x(k) represents a physical quantity without noise. Furthermore, m represents a measurement count, n represents the number of signals from the biological system, A represents an n×m matrix indicating a system model, and H represents an m×n matrix indicating a measurement system model. As indicated by equation (21), the physical quantity x(k+1) includes a physical quantity Ax(k) at previous time and biological system noise of $w_s(k)$. As indicated by equation (22), the system input u(k) includes a measured value Hx(k) and measurement system noise of $w_m(k)$. In this embodiment, the measured value Hx(k) is a phase value input from the feature amount extraction unit 30.

$$\hat{x}(k+1) = A\hat{x}(k) + K[u(k) - HA\hat{x}]  \quad (23)$$

Note that K(k) represents an n×m matrix indicating a Kalman gain, and x̂(k) represents the estimated value of the physical quantity x(k) (in this embodiment, the estimated value of the phase). The Kalman gain K(k) can be obtained by equations (24) to (26) below.

$$K(k) = \frac{P(k\,|\,k-1)H^T}{HP(k\,|\,k-1)H^T + R(k)} \quad (24)$$

$$P(k\,|\,k) = (1 - KH)P(k\,|\,k-1) \quad (25)$$

$$P(k+1\,|\,k) = AP(k\,|\,k)A^T + Q(k) \quad (26)$$

Note that R represents a covariance matrix relating to sensor noise, Q represents a covariance matrix relating to biological system noise, and P represents a covariance matrix relating to the estimated value. $H^T$ and $A^T$ are transposed matrices of matrices H and A, respectively. The Kalman gain K(k) is recursively determined so as to minimize the measurement system noise $w_m(k)$. The diagonal elements of the covariance matrix P(k|k) are squared estimation errors minimized by filter processing.

To accurately preset the covariance matrix R relating to sensor noise, using a time domain where the respiratory rate of the subject is stable, standard deviations σ in the time domain are calculated for the phase information of the R-wave amplitude, that of the R-R interval, and that of the angular displacement, all of which have been obtained by the feature amount extraction unit 30.

Under the assumption that the inputs of the R-wave amplitude, R-R interval, and angular displacement are independent of each other, the covariance matrix R is a diagonal matrix. The average value of the standard deviations σ obtained for the phase information of the R-wave amplitude is preset as diagonal elements of the covariance matrix R of the Kalman filter 31-1 for the R-wave amplitude, the average value of the standard deviations σ obtained for the phase information of the R-R interval is preset as the diagonal elements of the covariance matrix R of the Kalman filter 31-2 for the R-R interval, and the average value of the standard deviations σ obtained for the phase information of the angular displacement is preset as the diagonal elements of the covariance matrix R of the Kalman filter 31-3 for the angular displacement. It is considered that the covariance matrix R relating to sensor noise depends on a measurement environment but has no significant difference due to the individual difference.

On the other hand, the covariance matrix Q relating to biological system noise is biological system noise and reflects the individual difference. The covariance matrix Q is a diagonal matrix. As parameters that can change the diagonal elements of the covariance matrix Q, the optimal values of the diagonal elements of the covariance matrix Q are numerically tested for each subject, and the values of the diagonal elements are preset in accordance with the subject. As described above, when data are measured while making the subject breath and the covariance matrices R and Q are determined based on the measured data, the estimation accuracy of the phase can be improved. Each parameter will be exemplified. x(k) can be represented as a vector of a phase θk and $\dot{\theta}_k$. $\dot{\theta}_k$ is the differentiation of the phase θk. In this example, "•" above a letter will be referred to as "dot" hereinafter. Constants q1 and r1 of the covariance matrices Q and R are settable parameters, and are set, as described above. For example, $q1 = 1 \times 10^{-3}$ and $r1 = 2.4$.

$$x(k) = \begin{bmatrix} \theta_k \\ \dot{\theta}_k \end{bmatrix}$$

$$A = \begin{bmatrix} 1 & \Delta t \\ 0 & 1 \end{bmatrix}$$

$$H = \begin{bmatrix} 1 & 0 \end{bmatrix}$$

$$Q = \begin{bmatrix} 0 & 0 \\ 0 & q1 \end{bmatrix}$$

$$R = r1$$

The Kalman filter 31 (31-1 to 31-3) performs filter processing for each sampling period (in this embodiment, every second) of the sampling unit 28.

Figure 16:
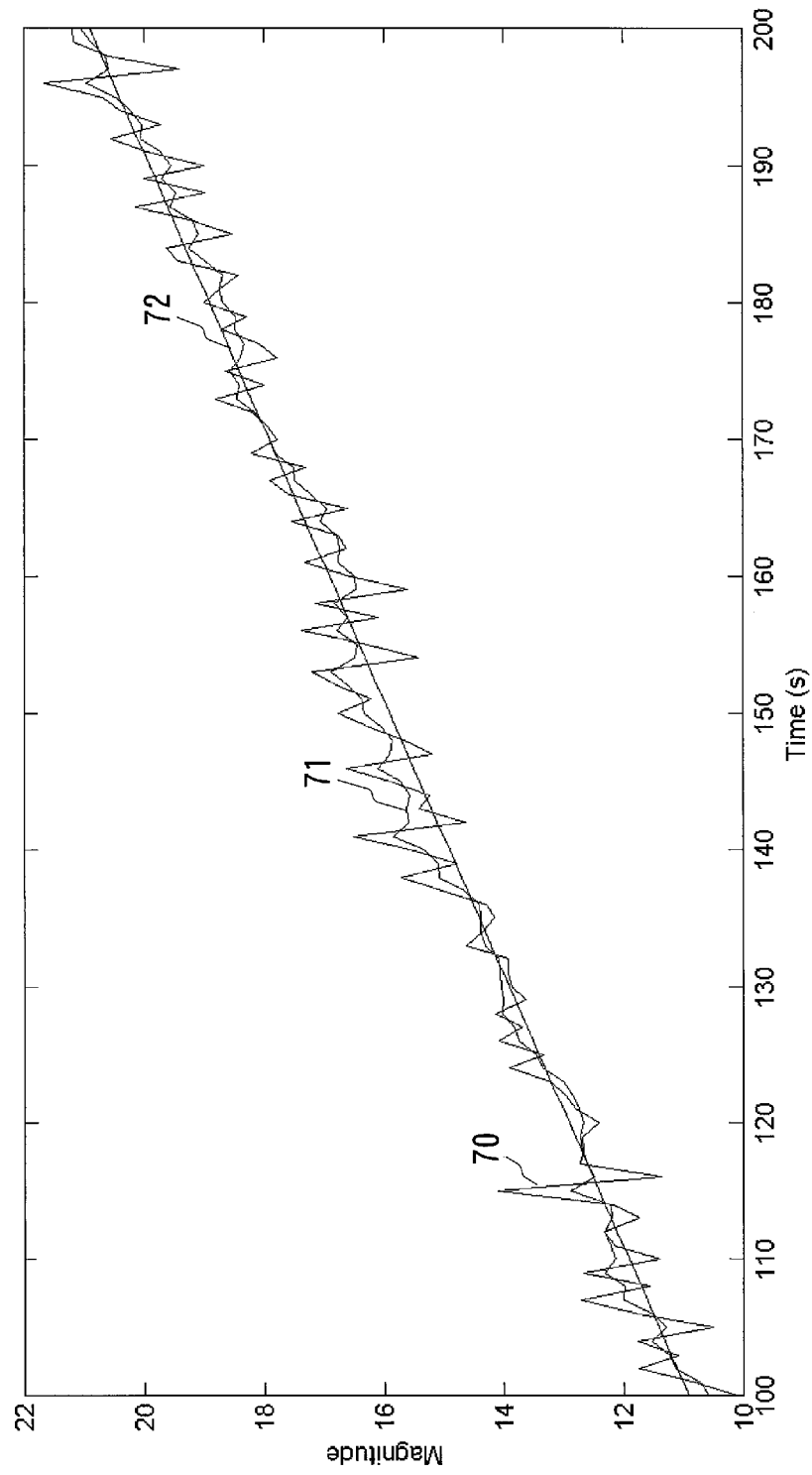
FIG. 16 is a timing chart showing an estimated phase after Kalman filter processing according to the second embodiment of the present invention.

FIG. 16 shows the estimated phase after the Kalman filter processing according to this embodiment. Reference numeral 70 denotes a measured value (phase value) input to the Kalman filter 31; 71, an estimated value (phase value) output from the Kalman filter 31; and 72, the ideal straight line of the phase. With respect to the measured value, the estimated value has a small error from the ideal straight line. While the measured value has a standard error of 0.5663 (rad), the estimated value after the filter processing has a standard error of 0.2711 (rad).

Figure 17:
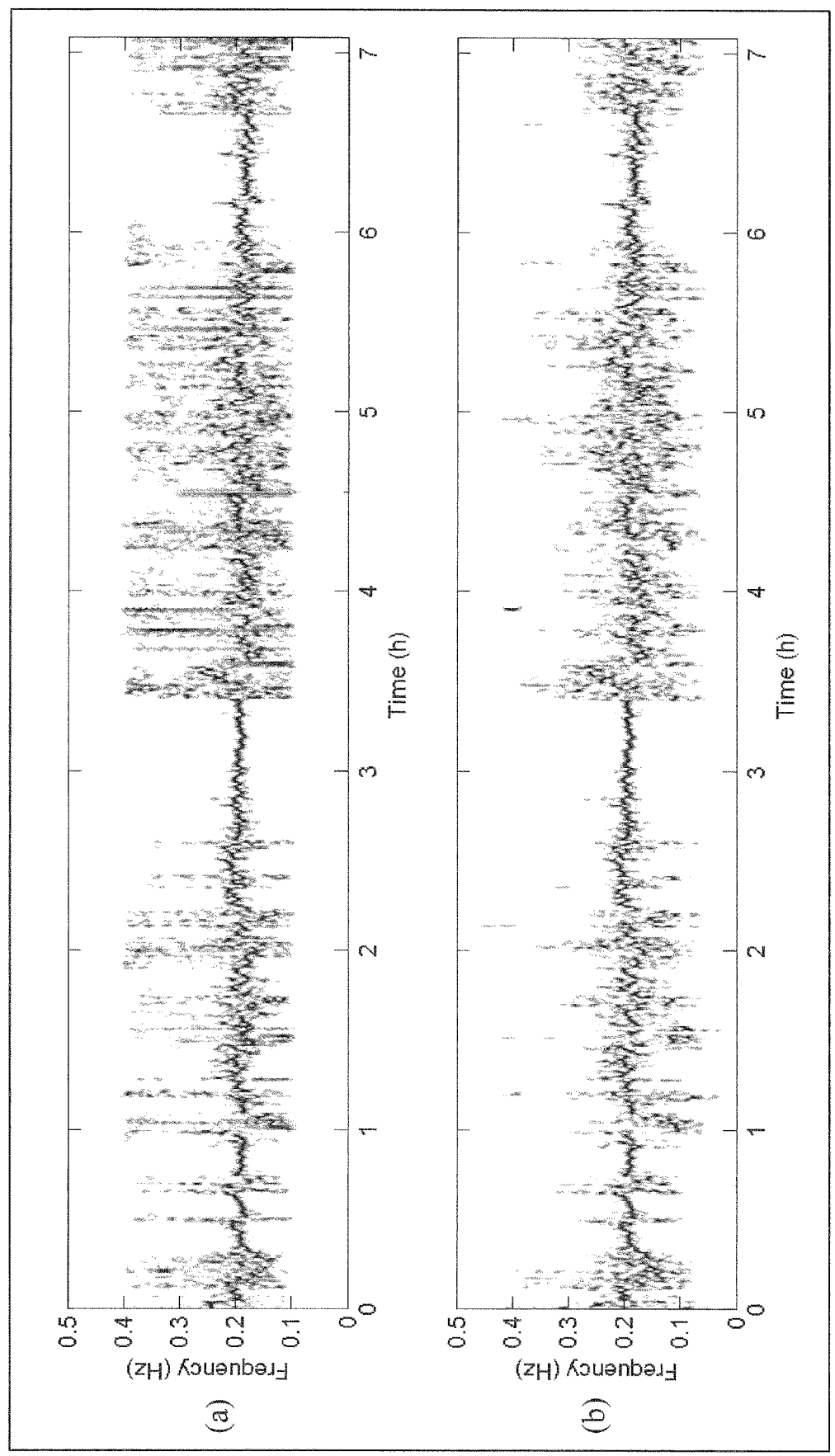
FIG. 17 shows timing charts respectively showing a respiration frequency signal string estimated based on phase information of an angular displacement and that estimated based on phase information obtained after applying Kalman filter processing to the phase information of the angular displacement.

In FIG. 17, (a) is a timing chart showing a respiration frequency signal string estimated based on the phase information of the angular displacement, and (b) is a timing chart showing a respiration frequency signal string estimated based on the phase information of the angular displacement after the Kalman filter processing. By comparing (a) and (b) of FIG. 17, it is found that by applying the Kalman filter processing, noise and fluctuation of a respiratory rate caused by the body motion of the subject or the like are reduced and the estimated value of the respiration frequency is stable.

The integration processing unit 32 integrates the data of the estimated phase values of the R-wave amplitude, R-R interval, and angular displacement by performing weighted averaging processing for the estimated phase value of the R-wave amplitude, that of the R-R interval, and that of the angular displacement, all of which have been obtained by the Kalman filters 31 (31-1 to 31-3), using weights based on squared estimation errors of the Kalman filters 31 (31-1 to 31-3) (step S309 of FIGS. 10 and 11).

Figure 18:
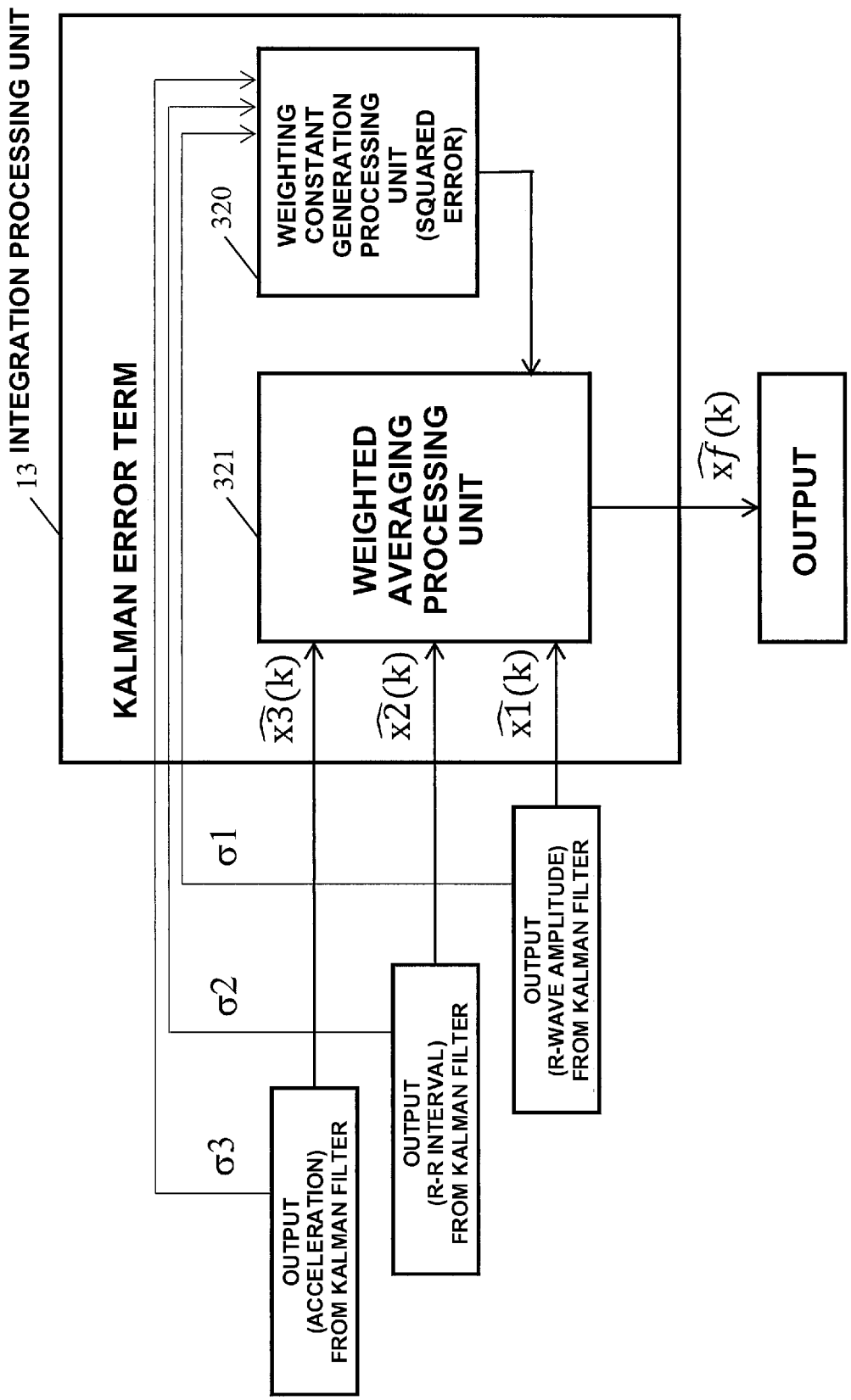
FIG. 18 is a block diagram showing the arrangement of an integration processing unit of the respiration estimation apparatus according to the second embodiment of the present invention.
Figure 19:
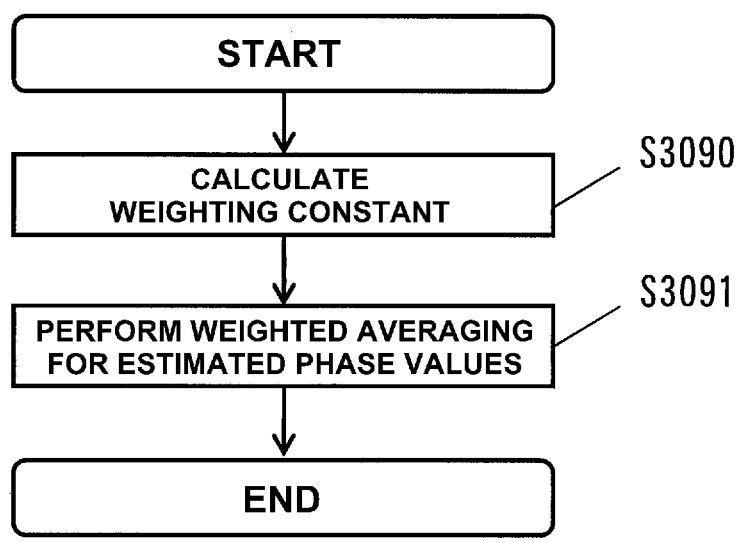
FIG. 19 is a flowchart for explaining a detailed operation of the integration processing unit of the respiration estimation apparatus according to the second embodiment of the present invention.

FIG. 18 is a block diagram showing the arrangement of the integration processing unit 32. FIG. 19 is a flowchart for explaining a detailed operation of the integration processing unit 32. The integration processing unit 32 includes a weighting constant generation processing unit 320 and a weighted averaging processing unit 321. In the above-described Kalman filter processing, the estimated phase values are obtained at each time (in this embodiment, every second), and the squared estimation errors are updated.

In this embodiment, σ1 represents the squared estimation error of the Kalman filter processing in the Kalman filter 31-1 for the R-wave amplitude, σ2 represents the squared estimation error of the Kalman filter processing in the Kalman filter 31-2 for the R-R interval, and σ3 represents the squared estimation error of the Kalman filter processing in the Kalman filter 31-3 for the angular displacement. The squared estimation error σi (i=1, 2, 3) of each of the R-wave amplitude, R-R interval, and angular displacement is given by the following equation.

$$\alpha i = E^{(\hat{x}(k) - x(k))} \quad (27)$$

The weighting constant generation processing unit 320 calculates the weighting constant αi from the squared estimation error σi of each of the R-wave amplitude, R-R interval, and angular displacement by equation (28) below (step S3090 of FIG. 19).

$$\alpha i = \frac{1/\sigma i^2}{1/\sigma 1^2 + 1/\sigma 2^2 + 1/\sigma 3^2} \quad (28)$$

The weighting constant generation processing unit 320 performs calculation by equation (28) for each of the R-wave amplitude, R-R interval, and angular displacement. Using the weighting constant αi (i=1, 2, 3) calculated by the weighting constant generation processing unit 320, the weighted averaging processing unit 321 calculates an integrated output value $\hat{x}f(k)$ as the phase value obtained by performing weighted averaging processing for an estimated phase value $\hat{x}1$ of the R-wave amplitude, an estimated phase value $\hat{x}2$ of the R-R interval, and an estimated phase value $\hat{x}3$ of the angular displacement by equation (29) below (step S3091 of FIG. 19).

$$\hat{x}_f(k) = \frac{\sum_i \alpha i \hat{x} i}{\alpha 1 + \alpha 2 + \alpha 3} \quad (29)$$

The integration processing unit 32 performs the above integration processing for each sampling period of the sampling unit 28 (in this embodiment, every second).

The respiration frequency conversion unit 33 converts the phase value integrated by the integration processing unit 32 into a frequency, and outputs a respiration frequency signal (step S310 of FIGS. 10 and 11). Since an instantaneous angular frequency is obtained by time-differentiating the phase value output from the integration processing unit 32, it is possible to obtain the respiration frequency by dividing the instantaneous angular frequency by 2π. Thus, the respiration frequency conversion unit 33 generates a respiration frequency signal string by arranging, in time-series, the data of the respiration frequencies, and outputs it.

Figure 20:
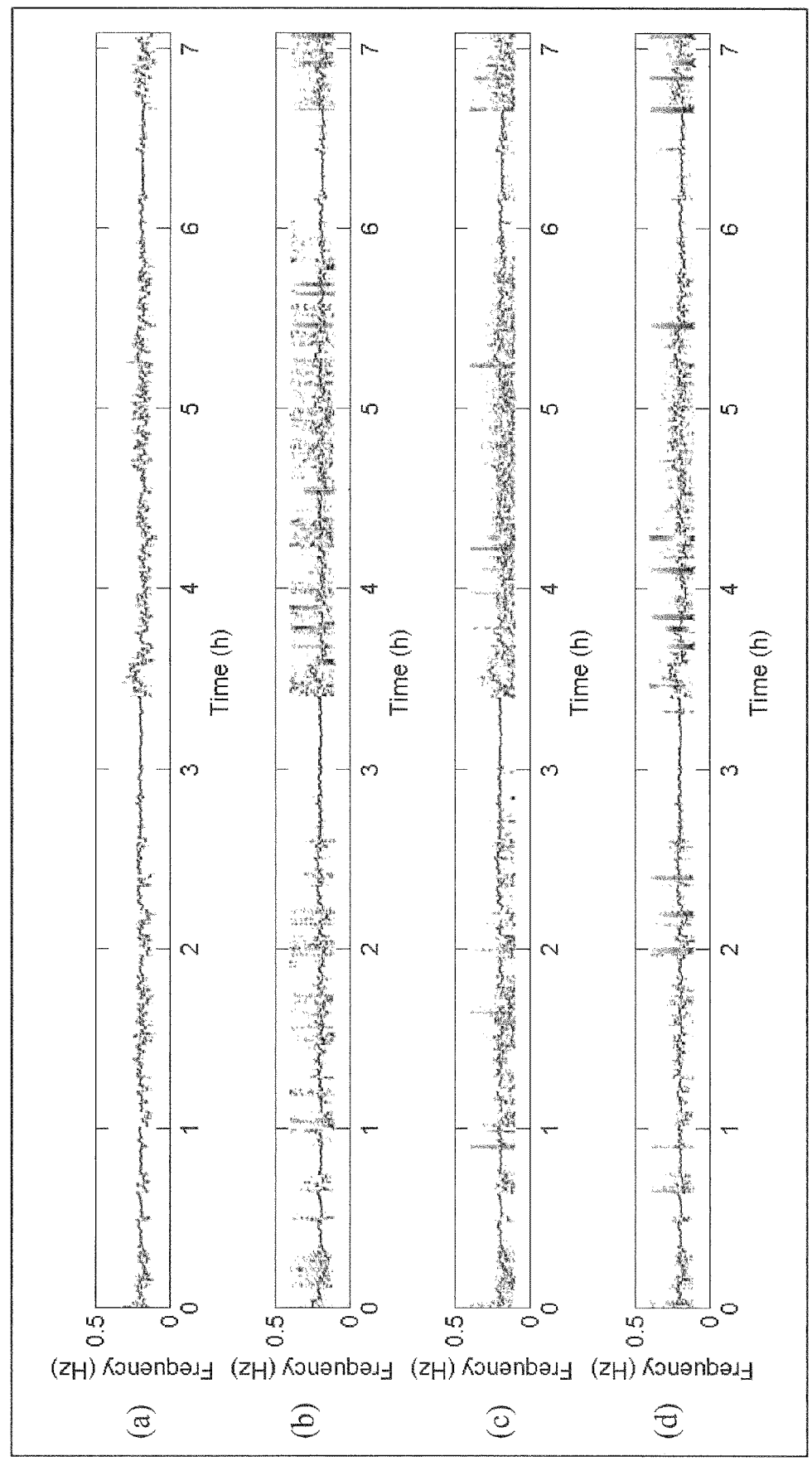
FIG. 20 shows timing charts respectively showing a respiration frequency signal string obtained by the respiration estimation apparatus according to the second embodiment of the present invention, and respiration frequency signal strings estimated based on pieces of phase information of an angular displacement, R-R interval, and R-wave amplitude after Kalman filter processing.

In FIG. 20, (a) is a timing chart showing a respiration frequency signal string obtained by the respiration estimation apparatus according to this embodiment, (b) is a timing chart showing a respiration frequency signal string estimated based on the phase information of the angular displacement after the Kalman filter processing, (c) is a timing chart showing a respiration frequency signal string estimated based on the phase information of the R-R interval after the Kalman filter processing, and (d) is a timing chart showing a respiration frequency signal string estimated based on the phase information of the R-wave amplitude after the Kalman filter processing.

According to this embodiment, the respiration frequency of the subject is estimated by integrating the plurality of sensor data and extracting the best data in order to cope with the individual difference of the age, autonomic nervous system, skin condition, and body structure of the subject.

When data of the triaxial acceleration is used to estimate the respiration frequency, it is difficult to exclude a measurement error caused by the individual difference of a body motion or body structure. When data of the R-R interval is used to estimate the respiration frequency, there is restriction on calculation of a respiration cycle by the cardiac cycle, and it is thus difficult to exclude a measurement error caused by the influence of the autonomic nervous system that changes depending on the mental condition and age. When data of the R-wave amplitude is used to estimate the respiration frequency, it is difficult to exclude a measurement error caused by the individual difference of the skin condition, a change in contact impedance in accordance with the body motion or skin condition, or the like. Conversely, in this embodiment, even if the S/N ratio degrades, it is possible to reduce noise of the respiration frequency and stably estimate the respiration frequency by integrating the plurality of sensor data.

The storage units 23 and 24, R-wave amplitude detection unit 25, R-R interval detection unit 26, acceleration displacement detection unit 27, sampling unit 28, bandpass filter 29, feature amount extraction unit 30, Kalman filter 31, integration processing unit 32, and respiration frequency conversion unit 33, all of which have been described in this embodiment, can be implemented by a computer including a CPU, a storage device, and an interface, and a program for controlling these hardware resources. The CPU executes the processing described in this embodiment in accordance with programs stored in the storage device.

The electrocardiograph 21 includes an electrode attached to clothing such as a shirt, and a cardiac potential waveform signal processing unit in a monitoring apparatus attached to the clothing, and the electrode and the cardiac potential waveform signal processing unit are connected by a wiring line. Similarly, the triaxial accelerometer 22 includes a sensor unit attached to the clothing and an acceleration signal processing unit provided in the monitoring apparatus, and the sensor unit and the acceleration signal processing unit are connected by a wiring line.

In this embodiment, the electrocardiograph 21 and the triaxial accelerometer 22 may be provided together with or separately from the wearable device attached to the clothing. That is, the storage units 23 and 24, R-wave amplitude detection unit 25, R-R interval detection unit 26, acceleration displacement detection unit 27, sampling unit 28, bandpass filter 29, feature amount extraction unit 30, Kalman filter 31, integration processing unit 32, and respiration frequency conversion unit 33 may be provided in the monitoring apparatus or provided in another apparatus.

When the storage units 23 and 24, R-wave amplitude detection unit 25, R-R interval detection unit 26, acceleration displacement detection unit 27, sampling unit 28, bandpass filter 29, feature amount extraction unit 30, Kalman filter 31, integration processing unit 32, and respiration frequency conversion unit 33 are provided in another apparatus, a cardiac potential waveform signal obtained by the electrocardiograph 21 and a triaxial acceleration signal obtained by the triaxial accelerometer 22 are wirelessly transmitted to the apparatus.

Figure 21:
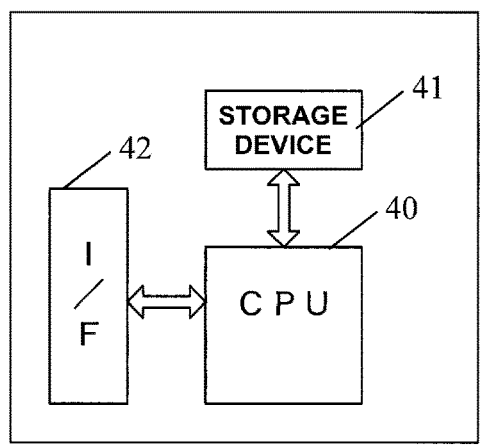
FIG. 21 is a block diagram showing an example of the arrangement of a computer that implements the respiration estimation apparatus according to the first and second embodiments of the present invention.
Figure 22:
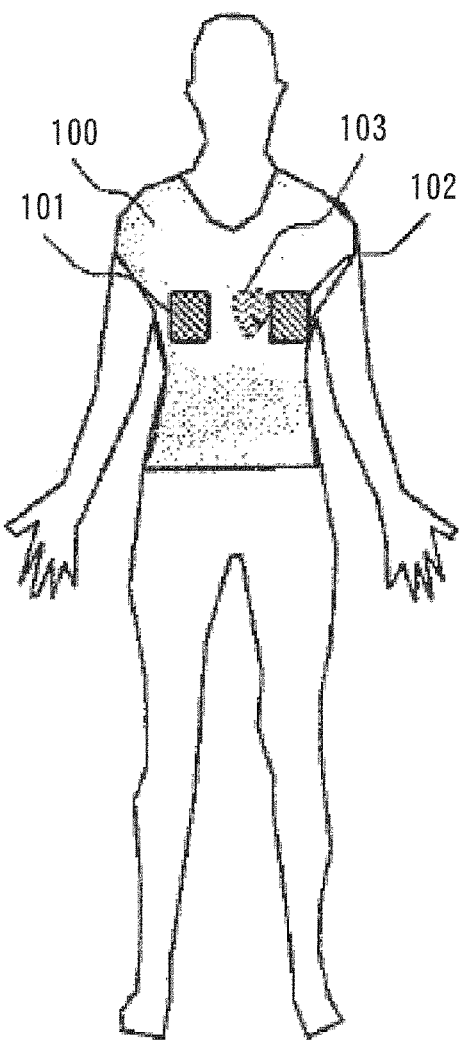
FIG. 22 is a schematic view showing a state in which a wearable sensor is mounted on a human body.

FIG. 21 shows an example of the arrangement of the computer described in the first and second embodiments. The computer includes a CPU 40, a storage device 41, and an interface device (to be referred to as an I/F hereinafter) 42. The I/F 42 is connected to the electrocardiograph 1 or 21, the triaxial accelerometer 2 or 22, and the like. In this computer, a program for implementing the respiration estimation method of the present invention is provided while being recorded on a recording medium such as a flexible disk, CD-ROM, DVD-ROM, or memory card, and stored in the storage device 41. The CPU 40 executes the processing described in the first or second embodiment in accordance with the program stored in the storage device 41.

The present invention is also applicable to a combination of data obtained from other sensors such as a magnetic field sensor and a microwave sensor without limitation to the combination of the axial accelerometer and the electrocardiograph.

The present invention has exemplified the R-wave amplitude and R-R interval as examples of data relating to the cardiac function of the subject. The use of the R-wave amplitude and R-R interval is not an essential arrangement requirement in the present invention. Another example of the data relating to the cardiac function includes the time-series signal of an S-wave amplitude or the time-series signal of an RS amplitude from the peak value of an R wave to that of an S wave. Note that the amplitude of the R wave is detected in the second embodiment while the RS amplitude is detected and the detection result is set as an R-wave amplitude in the first embodiment. Therefore, the R-wave amplitude detection unit 5 according to the first embodiment can be regarded as an RS amplitude detection unit. In the first embodiment, the R-wave amplitude detection unit 25 of the second embodiment may be used instead of the R-wave amplitude detection unit 5. Furthermore, when the S-wave amplitude is detected from the signal of the cardiac potential waveform, an S-wave amplitude detection unit is provided. Similarly to the case of the R wave, the S-wave amplitude detection unit can detect the S wave using a threshold. The S-wave amplitude detection unit detects an amplitude for each S wave of the cardiac potential waveform.

In the present invention, the three variables (the breathing rates in the first embodiment and the phase values in the second embodiment) obtained from the R-wave amplitude, R-R interval, and angular displacement are input to the Kalman filter 11 or 31. However, the preset invention is not limited to this. The present invention can be extended so that among variables obtained from the data relating to the cardiac function of the subject and a variable obtained from the acceleration data (angular displacement), two variables or four or more variables are input to the Kalman filter 11 or 31.

INDUSTRIAL APPLICABILITY

The present invention is applicable to continuous respiratory monitoring of continuously observing breathing of a person.

EXPLANATION OF THE REFERENCE NUMERALS AND SIGNS 1, 21 . . . electrocardiograph, 2, 22 . . . triaxial accelerometer, 3, 4, 23, 24 . . . storage unit, 5, 25 . . . R-wave amplitude detection unit, 6, 26 . . . R-R interval detection unit, 7, 27 . . . acceleration displacement detection unit, 8, 28 . . . sampling unit, 9, 29 . . . bandpass filter, 10 . . . breathing rate estimation unit, 11, 31 . . . Kalman filter, 12, 32 . . . integration processing unit, 13 . . . error measurement unit, 14 . . . weighting constant generation unit, 15 . . . adaptive estimation unit, 16 . . . weighting calculation unit, 30 . . . feature amount extraction unit, 33 . . . respiration frequency conversion unit, 120 . . . weighting constant generation processing unit, 121 . . . weighted averaging processing unit, 310 . . . Hilbert transform unit, 311 . . . angle calculation unit, 312 . . . unwrapping processing unit, 320 . . . weighting constant generation processing unit, 321 . . . weighted averaging processing unit

The invention claimed is:

1. A respiration estimation method comprising:
   a first step of estimating a breathing rate of a subject based on each of a time-series signal of first data relating to a cardiac function of the subject and a time-series signal of second data relating to an acceleration induced by a respiratory motion of the subject;
   a second step of estimating a breathing rate obtained by applying a Kalman filter to each of the breathing rate estimated based on the first data and the breathing rate estimated based on the second data to remove noise; and
   a third step of executing weighted averaging processing for estimated values of the breathing rates obtained in the second step wherein the first data includes at least one of an amplitude of an R wave, an R-R interval as an interval between an R wave and an immediately preceding R wave, an amplitude of an S wave, and an RS amplitude as an amplitude from a peak value of an R wave to a peak value of an S wave,
   the weighted average of the plurality of estimated values obtained after said third step is used for continuous respiratory monitoring of continuously observed breathing of the subject for at least one of a diagnosis of respiratory diseases, a rehabilitation of the subject with a respiratory disease, remote monitoring of a fetus subject and a subject stress diagnosis;
   a fourth step of measuring error coefficients respectively indicating reliabilities of the first data and the second data;
   a fifth step of obtaining weighting constants as elements of a weighting matrix based on the error coefficients;
   a sixth step of updating a covariance estimation error matrix of the Kalman filter so that an estimation error of the Kalman filter becomes minimum; and
   a seventh step of updating a Kalman Vain of the Kalman filter based on the weighting matrix and the covariance estimation error matrix using the weighted average processing results to monitor the subject for at least one said diagnosis of respiratory diseases, said rehabilitation of the subject with said respiratory disease, remote monitoring of said fetus subject and said subject stress diagnosis.

2. The respiration estimation method according to claim 1, wherein the first step includes
   a step of obtaining a frequency spectrum of each of the signals of the first data and the second data by Fourier-transforming each of the time-series signal of the first data and the time-series signal of the second data, and
   a step of estimating the breathing rate of the subject based on each of the frequency spectrum obtained from the first data and the frequency spectrum obtained from the second data.

3. The respiration estimation method according to claim 1, wherein the seventh step includes a step of adjusting a covariance matrix of measurement system noise in accordance with the weighting matrix, and calculating the Kalman gain using the adjusted covariance matrix.

4. The respiration estimation method according to claim 1, further comprising:
   a first detection step of detecting, as the first data, the amplitude of the R wave from a cardiac potential waveform of the subject;

a second detection step of detecting, as the first data, the R-R interval from the cardiac potential waveform of the subject; and
a third detection step of detecting, as the second data, an angular displacement of an acceleration vector from a triaxial acceleration signal by the respiratory motion of the subject.

5. A respiration estimation method comprising:
a first step of estimating a breathing rate of a subject based on each of a time-series signal of first data relating to a cardiac function of the subject and a time-series signal of second data relating to an acceleration induced by a respiratory motion of the subject,
a second step of estimating a breathing rate obtained by applying a Kalman filter to each of the breathing rate estimated based on the first data and the breathing rate estimated based on the second data to remove noise;
a third step of executing weighted averaging processing for estimated values of the breathing rates obtained in the second step wherein
the first data includes at least one of an amplitude of an R wave, an R-R interval as an interval between an R wave and an immediately preceding R wave, an amplitude of an S wave, and an RS amplitude as an amplitude from a peak value of an R wave to a peak value of an S wave,
the weighted average of the plurality of estimated values obtained after said third step is used for continuous respiratory monitoring of continuously observed breathing of the subject for at least one of a diagnosis of respiratory diseases, a rehabilitation of the subject with a respiratory disease, remote monitoring of a fetus subject and a subject stress diagnosis;
a fourth step of measuring error coefficients respectively indicating reliabilities of the first data and the second data;
a fifth step of obtaining weighting constants as elements of a weighting matrix based on the error coefficients;
a sixth step of updating a covariance estimation error matrix of the Kalman filter so that an estimation error of the Kalman filter becomes minimum, and
a seventh step of updating a Kalman gain of the Kalman filter based on the weighting matrix and the covariance estimation error matrix, wherein the third step includes
a step of calculating a weighting constant used in the weighted averaging processing based on a squared estimation error of the Kalman filter with respect to each of the first data and the second data, and
a step of performing weighted averaging for the estimated value of the breathing rate based on the first data and the estimated value of the breathing rate based on the second data using the weighting constant calculated in the step of calculating,
using the weighted average processing results to monitor the subject for at least one said diagnosis of respiratory diseases, said rehabilitation of the subject with said respiratory disease, remote monitoring of said fetus subject and said subject stress diagnosis.

6. A respiration estimation apparatus comprising:
a breathing rate estimator configured to estimate a breathing rate of a subject based on each of a time-series signal of first data relating to a cardiac function of the subject and a time-series signal of second data relating to an acceleration induced by a respiratory motion of the subject;
a Kalman filter which is applied to each of the breathing rate estimated based on the first data and the breathing rate estimated based on the second data; and
an integration processor configured to execute weighted averaging processing for estimated values of the breathing rates obtained by the Kalman filter, wherein
the weighted average of estimated values obtained by said weighted average processing is used for continuous respiratory monitoring of continuously observed breathing of the subject for at least one of a diagnosis of respiratory diseases, a rehabilitation of the subject with a respiratory disease, remote monitoring of a fetus subject and a subject stress diagnosis, wherein
the first data includes at least one of an amplitude of an R wave, an R-R interval as an interval between an R wave and an immediately preceding R wave, an amplitude of an S wave, and an RS amplitude as an amplitude from a peak value of an R wave to a peak value of an S wave,
an error detector step of measuring error coefficients respectively indicating reliabilities of the first data and the second data, a weighting constant generator step of obtaining weighting constants as elements of a weighting matrix based on the error coefficients;
an adaptive estimator step of updating a covariance estimation error matrix of the Kalman filter so that an estimation error of the Kalman filter becomes minimum, and
a weighting calculator step of updating a Kalman gain of the Kalman filter based on the weighting matrix and the covariance estimation error matrix,
wherein the respiration estimation apparatus is configured to monitor for at least one of said continuous respiratory monitoring of continuously observed breathing of the subject for at least one of said diagnosis of respiratory diseases, said rehabilitation of the subject with said respiratory disease, remote monitoring of said fetus subject and said subject stress diagnosis,
using the weighted average processing results to monitor the subject for at least one said diagnosis of respiratory diseases, said rehabilitation of the subject with said respiratory disease, remote monitoring of said fetus subject and said subject stress diagnosis.

7. A respiration estimation method comprising:
a first step of extracting phase information from each of a time-series signal of first data relating to a cardiac function of a subject and a time-series signal of second data relating to an acceleration induced by a respiratory motion of the subject;
a second step of estimating phase information obtained by applying a Kalman filter to each of the phase information of the first data and the phase information of the second data to remove noise;
a third step of executing weighted averaging processing for estimated phase values obtained in the second step;
a fourth step of obtaining a respiration frequency of the subject by converting, into a frequency, a phase value integrated in the third step, wherein
the respiration frequency of the subject obtained after said fourth step is used for continuous respiratory monitoring of continuously observed breathing of the subject for at least one of a diagnosis of respiratory diseases, a rehabilitation of the subject with a respiratory disease, remote monitoring of a fetus subject and a subject stress diagnosis, wherein
the first data includes at least one of an amplitude of an R wave, an R-R interval as an interval between an R wave and an immediately preceding R wave, an amplitude of an S wave, and an RS amplitude as an amplitude from a peak value of an R wave to a peak value of an S wave, and wherein the third step includes
a step of calculating a weighting constant from a squared estimation error of the Kalman filter with respect to each of the first data and the second data, and
a step of executing weighted averaging processing for the estimated phase value of the first data and the estimated phase value of the second data using the weighting constants calculated in the step of calculating the weighting constant,
using the weighted average processing results to monitor the subject for at least one said diagnosis of respiratory diseases, said rehabilitation of the subject with said respiratory disease, remote monitoring of said fetus subject and said subject stress diagnosis.

8. The respiration estimation method according to claim 7, wherein the first step includes
a step of generating two signal components of a real-part component and an imaginary-part component by Hilbert-transforming the time-series signal with respect to each of the first data and the second data,
a step of calculating an angle from the real-part component and the imaginary-part component with respect to each of the first data and the second data, and
a step of performing phase unwrapping for converting the angle into continuous phase values with respect to each of the first data and the second data.

9. The respiration estimation method according to claim 7, further comprising:
a fifth step of sampling each of the time-series signal of the first data and the time-series signal of the second data at a sampling frequency lower than a sampling frequency of a cardiac potential waveform and a sampling frequency of a triaxial acceleration signal; and
a sixth step of limiting a band of each of the time-series signal of the first data and the time-series signal of the second data, both of which have been acquired in the fifth step,
wherein the first step includes a step of extracting phase information from each of the time-series signal of the first data and the time-series signal of the second data, in which each the band has been limited in the sixth step.

10. The respiration estimation method according to claim 7, further comprising:
a first detection step of detecting, as the first data, an amplitude of an R wave from a cardiac potential waveform of the subject;
a second detection step of detecting, as the first data, an R-R interval as an interval between an R wave and an immediately preceding R wave from the cardiac potential waveform of the subject; and
a third detection step of detecting, as the acceleration data, an angular displacement of an acceleration vector from a triaxial acceleration signal by the respiratory motion of the subject.

11. A respiration estimation apparatus comprising:
a feature amount attractor configured to attract phase information from each of a time-series signal of first data relating to a cardiac function of a subject and a time-series signal of second data relating to an acceleration induced by a respiratory motion of the subject;
a Kalman filter which is applied to each of the phase information of the first data and the phase information of the second data, both of which have been obtained by the feature amount extraction unit;
an integration processor configured to execute weighted averaging processing for an estimated phase value of the first data and an estimated phase value of the second data, both of which have been obtained by the Kalman filter; and
a respiration frequency convertor configured to obtain a respiration frequency of the subject by converting, into a frequency, a phase value integrated by the integration processing unit, wherein
the respiration frequency of the subject obtained from said respiration frequency converter is used for continuous respiratory monitoring of continuously observed breathing of the subject for at least one of a diagnosis of respiratory diseases, a rehabilitation of the subject with a respiratory disease, remote monitoring of a fetus subject and a subject stress diagnosis, wherein
the first data includes at least one of an amplitude of an R wave, an R-R interval as an interval between an R wave and an immediately preceding R wave, an amplitude of an S wave, and an RS amplitude as an amplitude from a peak value of an R wave to a peak value of an S wave, and
wherein the integration processor step includes
a weighting constant generation processor step of calculating a weighting constant from a squared estimation error of the Kalman filter with respect to each of the first data and the second data, and
a weighting averaging processor step of executing weighted averaging processing for the estimated phase value of the first data and the estimated phase value of the second data using the weighting constants calculated in the step of calculating the weighting constant, wherein the respiration estimation apparatus is configured to monitor for at least one of said continuous respiratory monitoring of continuously observed breathing of the subject for at least one of said diagnosis of respiratory diseases, said rehabilitation of the subject with said respiratory disease, remote monitoring of said fetus subject and said subject stress diagnosis.

* * * * *